(12) United States Patent
van de Ven

(10) Patent No.: US 9,681,510 B2
(45) Date of Patent: Jun. 13, 2017

(54) LIGHTING DEVICE WITH OPERATION RESPONSIVE TO GEOSPATIAL POSITION

(71) Applicant: Cree, Inc., Durham, NC (US)

(72) Inventor: Antony Paul van de Ven, Sai Kung (HK)

(73) Assignee: Cree, Inc., Durham, NC (US)

(*) Notice: Subject to any disclaimer, the term of this patent is extended or adjusted under 35 U.S.C. 154(b) by 0 days.

(21) Appl. No.: 14/669,739

(22) Filed: Mar. 26, 2015

(65) Prior Publication Data

US 2016/0286616 A1 Sep. 29, 2016

(51) Int. Cl.
*H05B 33/08* (2006.01)
*H05B 37/02* (2006.01)
*A61N 5/06* (2006.01)

(52) U.S. Cl.
CPC ....... *H05B 33/0842* (2013.01); *A61N 5/0618* (2013.01); *H05B 37/0218* (2013.01); *H05B 37/0227* (2013.01); *H05B 37/0245* (2013.01); *H05B 37/0281* (2013.01); *A61N 2005/0626* (2013.01); *A61N 2005/0651* (2013.01); *Y02B 20/42* (2013.01)

(58) Field of Classification Search
CPC ........... H05B 37/0227; H05B 37/0245; H05B 37/0272; H05B 37/02; H05B 33/0854; H05B 33/0842; H05B 33/0863; H05B 37/0218; H05B 37/0254
See application file for complete search history.

(56) References Cited

U.S. PATENT DOCUMENTS

| 5,803,579 A | 9/1998 | Turnbull et al. |
| 6,150,774 A | 11/2000 | Mueller et al. |
| 6,234,648 B1 | 5/2001 | Börner et al. |
| 6,357,889 B1 | 3/2002 | Duggal et al. |
| 6,441,558 B1 | 8/2002 | Muthu et al. |

(Continued)

FOREIGN PATENT DOCUMENTS

| JP | 2008264430 A | 11/2008 |
| JP | 2009152213 A | 7/2009 |

(Continued)

OTHER PUBLICATIONS

U.S. Appl. No. 14/260,048, filed Apr. 23, 2014.
(Continued)

*Primary Examiner* — Jany Richardson
(74) *Attorney, Agent, or Firm* — Withrow & Terranova, P.L.L.C.; Vincent K. Gustafson

(57) ABSTRACT

A lighting device is arranged to receive or determine information indicative of geospatial location (and optionally additional information such as time, time zone, and/or date) and automatically adjust one or more light output parameters (e.g., luminous flux, color point, color temperature, spectral content, and operating time) based on such information to operate one or more emitters differently on different days of a year. Information indicative of geospatial location may be received or provided by a user input element, a signal receiver, and/or at least one sensor. Brightness and/or spectral content of lighting device emissions may be further adjusted intraday based on sensed ambient conditions, conditions of an illuminated space or surface, information indicative of weather conditions, and/or user inputs.

35 Claims, 16 Drawing Sheets

(56) References Cited

U.S. PATENT DOCUMENTS

| | | |
|---|---|---|
| 6,498,440 B2 | 12/2002 | Stam et al. |
| 6,577,073 B2 | 6/2003 | Shimizu et al. |
| 6,600,175 B1 | 7/2003 | Baretz et al. |
| 6,788,011 B2 | 9/2004 | Mueller et al. |
| 7,005,679 B2 | 2/2006 | Tarsa et al. |
| 7,026,756 B2 | 4/2006 | Shimizu et al. |
| 7,095,056 B2 | 8/2006 | Vitta et al. |
| 7,213,940 B1 | 5/2007 | Van De Ven et al. |
| 7,233,831 B2 | 6/2007 | Blackwell |
| 7,255,457 B2 | 8/2007 | Ducharme et al. |
| 7,257,551 B2 | 8/2007 | Oskorep et al. |
| 7,344,279 B2 | 3/2008 | Mueller et al. |
| 7,352,138 B2 | 4/2008 | Lys et al. |
| 7,354,172 B2 | 4/2008 | Chemel et al. |
| 7,358,679 B2 | 4/2008 | Lys et al. |
| 7,385,359 B2 | 6/2008 | Dowling et al. |
| 7,520,634 B2 | 4/2009 | Ducharme et al. |
| 7,564,180 B2 | 7/2009 | Brandes |
| 7,687,753 B2 | 3/2010 | Ashdown |
| 7,744,242 B2 | 6/2010 | Krämer |
| 7,768,192 B2 | 8/2010 | Van De Ven et al. |
| 7,781,953 B2 | 8/2010 | Su |
| 7,824,065 B2 | 11/2010 | Maxik |
| 7,828,460 B2 | 11/2010 | Van De Ven et al. |
| 7,828,463 B1 | 11/2010 | Willis |
| 7,845,823 B2 | 12/2010 | Mueller et al. |
| 7,918,581 B2 | 4/2011 | Van De Ven et al. |
| 7,999,491 B2 | 8/2011 | Peng et al. |
| 8,038,317 B2 | 10/2011 | Van De Ven et al. |
| 8,201,966 B2 | 6/2012 | Hall et al. |
| 8,258,722 B2 | 9/2012 | Swoboda et al. |
| 8,362,707 B2 | 1/2013 | Draper et al. |
| 8,436,556 B2 | 5/2013 | Eisele et al. |
| 8,508,127 B2 | 8/2013 | Negley et al. |
| 8,593,074 B2 | 11/2013 | Hatley et al. |
| 8,686,641 B2 | 4/2014 | Maxik et al. |
| 8,796,951 B2 | 8/2014 | Feri et al. |
| 9,024,536 B2 | 5/2015 | Maxik et al. |
| 9,039,746 B2 | 5/2015 | van de Ven et al. |
| 9,192,013 B1 | 11/2015 | van de Ven et al. |
| 9,241,384 B2 | 1/2016 | van de Ven et al. |
| 2003/0090210 A1 | 5/2003 | Bierman |
| 2004/0218387 A1 | 11/2004 | Gerlach |
| 2005/0236998 A1 | 10/2005 | Mueller et al. |
| 2006/0106437 A1 | 5/2006 | Czeisler et al. |
| 2006/0149607 A1 | 7/2006 | Sayers et al. |
| 2007/0223219 A1 | 9/2007 | Medendorp, Jr. et al. |
| 2008/0179611 A1 | 7/2008 | Chitnis et al. |
| 2008/0215279 A1 | 9/2008 | Salsbury et al. |
| 2009/0034258 A1 | 2/2009 | Tsai et al. |
| 2009/0079846 A1 | 3/2009 | Chou |
| 2009/0184616 A1 | 7/2009 | Van De Ven et al. |
| 2009/0296384 A1 | 12/2009 | Van De Ven et al. |
| 2010/0084996 A1 | 4/2010 | Van De Sluis et al. |
| 2010/0127283 A1 | 5/2010 | van de Ven et al. |
| 2010/0254129 A1 | 10/2010 | Le Toquin et al. |
| 2010/0277907 A1 | 11/2010 | Phipps et al. |
| 2010/0301773 A1 | 12/2010 | Chemel et al. |
| 2011/0084614 A1* | 4/2011 | Eisele ............... H05B 33/0857 |
| | | 315/152 |
| 2011/0175510 A1 | 7/2011 | Rains, Jr. et al. |
| 2011/0282468 A1 | 11/2011 | Ashdown |
| 2012/0038291 A1 | 2/2012 | Hasnain |
| 2012/0306355 A1 | 12/2012 | Seibel, II |
| 2012/0306375 A1 | 12/2012 | van de Ven |
| 2013/0063042 A1 | 3/2013 | Bora et al. |
| 2013/0114241 A1 | 5/2013 | van de Ven et al. |
| 2013/0271991 A1 | 10/2013 | Hussell et al. |
| 2014/0028219 A1 | 1/2014 | Chen et al. |
| 2014/0042910 A1 | 2/2014 | Chan |
| 2014/0052220 A1 | 2/2014 | Pedersen |
| 2014/0152188 A1 | 6/2014 | Bora et al. |
| 2014/0166447 A1* | 6/2014 | Thea ..................... H01H 43/02 |
| | | 200/19.01 |
| 2014/0228914 A1 | 8/2014 | van de Ven et al. |
| 2014/0292206 A1* | 10/2014 | Lashina ................ H05B 37/02 |
| | | 315/149 |
| 2014/0306620 A1 | 10/2014 | Maxik et al. |
| 2015/0002030 A1 | 1/2015 | McRae |
| 2015/0021465 A1 | 1/2015 | Gettings et al. |
| 2015/0161137 A1* | 6/2015 | Lashina .............. G06F 17/3053 |
| | | 707/749 |
| 2015/0216016 A1* | 7/2015 | Reed .................. H05B 37/0218 |
| | | 315/159 |
| 2015/0257243 A1* | 9/2015 | Saffari ............... H05B 37/0272 |
| | | 315/113 |
| 2016/0366746 A1 | 12/2016 | van de Ven et al. |

FOREIGN PATENT DOCUMENTS

| | | |
|---|---|---|
| WO | 0034709 A1 | 6/2000 |
| WO | 2009041171 A1 | 4/2009 |
| WO | 2013085978 A2 | 6/2013 |
| WO | 2014165692 A1 | 10/2014 |
| WO | 2015049146 A1 | 4/2015 |

OTHER PUBLICATIONS

U.S. Appl. No. 14/298,229, filed Jun. 6, 2014.
Negley, G. et al., "Essentials of designing efficient luminaires with LEDs," LEDs Magazine, Issue 18, Jan./Feb. 2008, Pennwell Corporation, pp. 17-22.
Van De Ven, A. et al., "Warm White illumination with high CRI and high efficacy by combining 455nm excited yellowish phosphor LEDs and red AlInGaP LEDs," The First International Conference on White LEDs and Solid State Lighting, Nov. 28, 2007, Led Lighting Fixtures, Inc., 8 pages.
Duffy, Jeanne F. et al., "Effect of Light on Human Circadian Physiology," Sleep Medicine Clinics, Jun. 2009, vol. 4, Issue 2, Elsevier Inc., pp. 1-18.
Rea, Mark S. et al., "Circadian Light," Journal of Circadian Rhythms, vol. 8, Issue 2, Feb. 2010, 10 pages.
Author Unknown, "Marvell 88MB300 Bluetooth Microcontroller: Bluetooth 4.1 Low Energy (LE) Dual Mode System-on-Chip (SoC)," Internet of Things (IoT), 2014, Marvell Technology Group Ltd., 2 pages.
Author Unknown, "RN4020: Bluetooth® Low Energy Module," Advance Information, Mar. 25, 2014, Microchip Technology Inc., DS50002279A-p. 1 to DS50002279A-p. 26.
Rea, M.S., et al., "White lighting for residential applications," Lighting Research and Technology, vol. 45, Issue 3, 2013, The Chartered Institution of Building Services Engineers, pp. 331-344.
Walker, Rick, "Lighting using Smart Mesh," CSR Confidential, Aug. 2013, Cambridge Silicon Radio Limited, 25 pages.
Invitation to Pay Additional Fees and Partial International Search for International Patent Application No. PCT/IB2016/053454, mailed Sep. 15, 2016, 8 pages.
International Search Report and Written Opinion for International Patent Application No. PCT/IB2016/053454, mailed Jan. 19, 2017, 19 pages.
MacAdam, David, L., "Visual Sensitivities to Color Differences in Daylight," Journal of the Optical Society of America, vol. 32, Issue 5, May 1942, Optical Society of America, pp. 247-274.
Non-Final Office Action for U.S. Appl. No. 15/179,658, mailed Mar. 10, 2017, 15 pages.

* cited by examiner

| Daylight Sources | Color Temperature |
|---|---|
| Overcast Sky | 7000 |
| Noon Sun / Clear Summer Sky | 5000 to 7000 |
| Noon Sun / Clear Winter Sky | 5500 to 6000 |
| Noon Sunlight (Date Dependent) | 4900 to 5800 |
| Average Noon Sunlight (Northern Hemisphere) | 5400 |
| Sunlight at 30-Degree Altitude | 4500 |
| Sunlight at 20-Degree Altitude | 4000 |
| Sunlight at 10-Degree Altitude | 3500 |
| Sunrise and Sunset | 3000 |

*FIG. 2*

| Time of Day | Dawn to mid-morning | Mid-day | Afternoon | Mid-afternoon to evening | Late evening to bedtime | Midnight to dawn |
|---|---|---|---|---|---|---|
| Ambient light | Increasing intensity, horizontal | Very high intensity, vertical | Very high intensity, mostly vertical | Decreasing intensity | Low to none | Low to none |
| Desired aptitude | Waking up, becoming alert | Alert | Alert | Alert to relaxed | Relaxed, sleepy | Sleeping; melatonin active; night vision |
| Possible artificial light level | High > 100 | High >100 | High >100 | Medium ~25 | Low < 10 | Very low < 1 |
| Possible artificial light CCT | High (cool) >6500K | High (cool) 3500 to 5000K | High (cool) 4000K to 5000K | Medium (neutral) 3500K to 4500K | Low (warm) 2000K to 3000K | Very low < 1500K |

*FIG. 3*

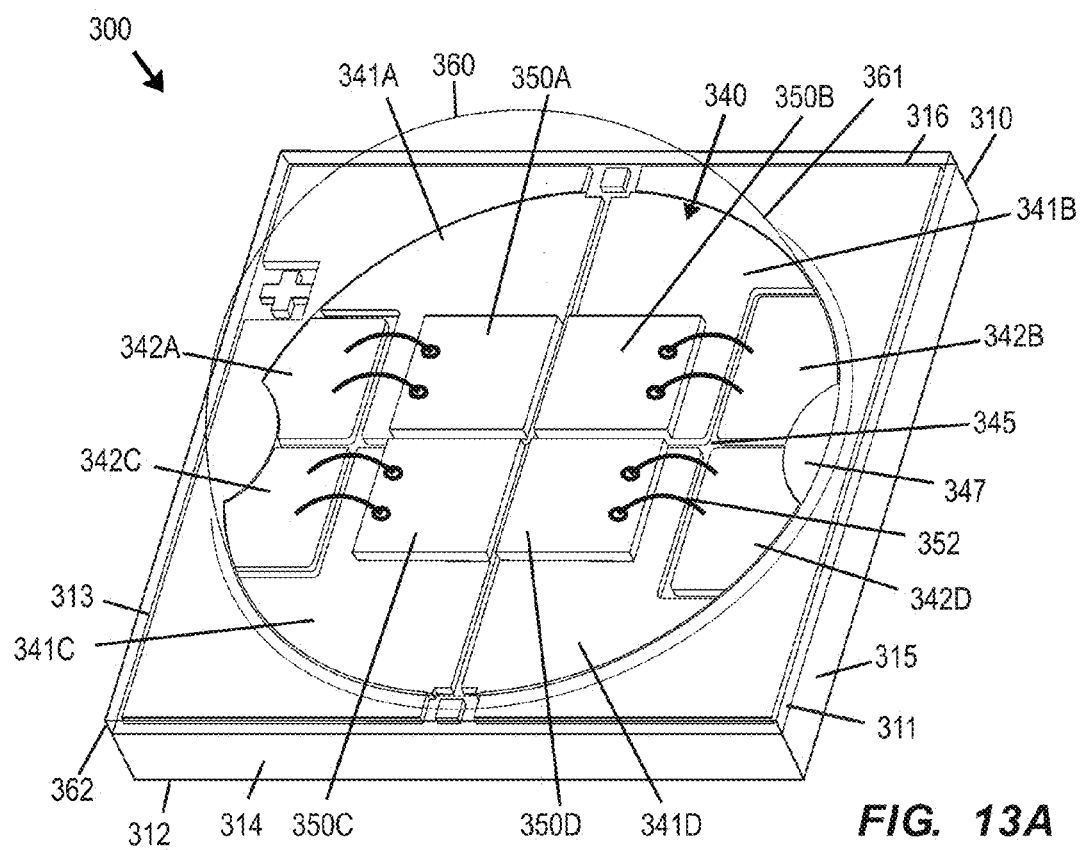
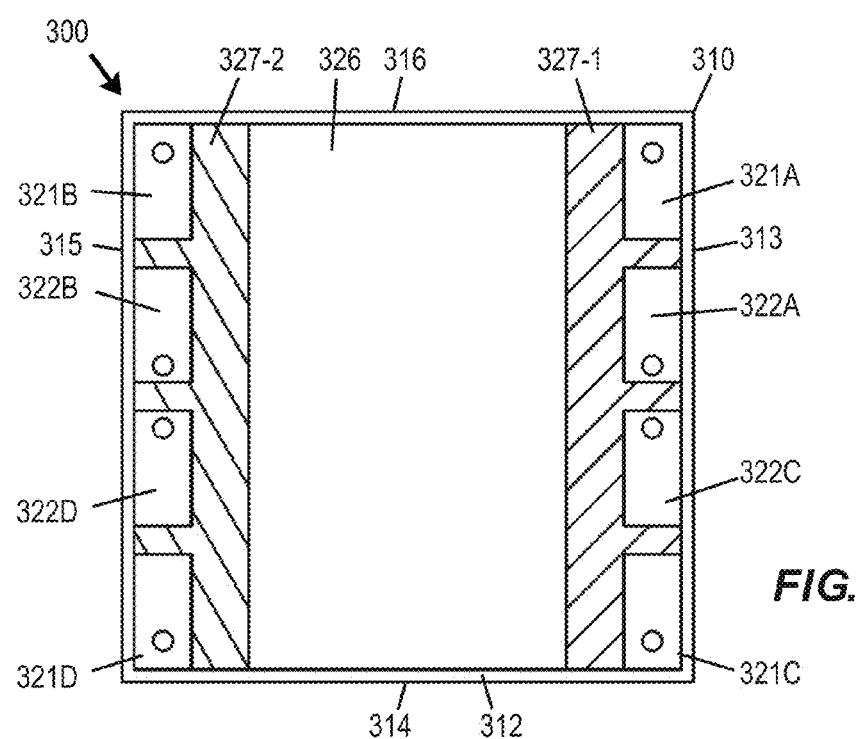
FIG. 13A
FIG. 13B

LIGHTING DEVICE WITH OPERATION RESPONSIVE TO GEOSPATIAL POSITION

TECHNICAL FIELD

Subject matter herein relates to lighting devices, including devices with one or more emitters or groups of emitters being controllable to provide desired effects, and relates to associated methods of making and using such devices.

BACKGROUND

Combining light sources of different spectra permit lighting devices to emit a light spectrum of almost any desired energy content. For example, red light can be combined with unsaturated green light to yield a light spectrum that renders colors similar to daylight or similar to incandescence depending on the amount of accompanying blue light. Using red, green, and blue light sources, colors from such sources can be combined in any proportion to yield any aggregate color within the gamut of colors.

Color is the visual effect that is caused by the spectral composition of the light emitted, transmitted, or reflected by objects. Human vision is primarily related to color and brightness (contrast) of the light source, and (if reflected light is present) the spectrum that is reflected from an object being illuminated.

As a heated object becomes incandescent, it first glows reddish, then yellowish, then white, and finally bluish. Thus, apparent colors of incandescing materials are directly related to their actual temperature (in Kelvin (K)). Practical materials that incandesce are said to have correlated color temperature (CCT) values that are directly related to color temperatures of blackbody sources. CCT is measured in Kelvin (K) and defined by the Illuminating Engineering Society of North America (IESNA) as "the absolute temperature of a blackbody whose chromaticity most nearly resembles that of the light source." Light having a CCT below 3200K is yellowish white in character and is generally considered to be warm white light, whereas light between having a CCT between 3200K and 4000K is generally considered to be neutral white light, and light having a CCT above 4000K is bluish white in character and generally considered to be cool white light.

It is important that lighting be of appropriate intensity for the task at hand and also have appropriate color rendering characteristics. For most daytime tasks, light sources (whether artificial or natural) should have high intensity and high color rendering. Conversely, for sleeping, light should have very low levels. The color differentiation of night vision is very low.

Light affects circadian rhythms. Human physiology responds non-visually to the presence or absence of certain wavelengths. For example, blue light is known to suppress melatonin, and ultraviolet rays are known to damage the skin. The intensity of light and the spectral content of light have a strong effect on the human circadian rhythms. These circadian rhythms are ideally synchronized with the natural light.

Circadian rhythm disorders may be associated with change in nocturnal activity (e.g., nighttime shift workers), change in longitude (e.g., jet lag), and/or seasonal change in light duration (e.g., seasonal affective disorder, with symptoms including depression). In 2007, the World Health Organization named late night shift work as a probable cancer-causing agent. Melatonin is an anti-oxidant and suppressant of tumor development; accordingly, interference with melatonin levels may increase the likelihood of developing cancer. Methods involving stimulus with artificial light sources to modify the phase and amplitude of a human circadian cycle (e.g., for resetting purposes) have been developed, such as disclosed in U.S. Patent Application Publication No. 2006/0106437A1 to Czeisler et al.

Artificial light sometimes includes too much blue light in the evening, which suppresses melatonin and hinders restful sleep. It is principally blue light (e.g., including blue light at a peak wavelength value between 460 to 480 nm, with some activity from about 360 nm to about 600 nm), that suppresses melatonin and synchronizes the circadian clock, proportional to the light intensity and length of exposure. Exposure to artificial light during the night may inhibit a person from falling to sleep or returning to sleep, and may also cause a temporary loss of night vision.

Natural light varies with respect to intensity and/or color temperature depending on the season, latitude, altitude, time of day, and weather conditions. Natural light variation due to season and geographic location may be understood with reference to FIG. 1, which plots hours of daylight per day as a function of latitude and time of year. Natural light also varies each day with respect to intensity and color temperature. The changing color temperature of sunlight over the course of the day is mainly a result of scattering of light, rather than changes in black-body radiation. Ignoring variations due to weather conditions, natural light intensity typically is low at sunrise, increases through mid-morning to a high level at mid-day, and then decreases in mid-afternoon to evening to a low level at sunset. Color temperature also varies in a predicable manner. During sunrise and sunset, color temperature tends to be around 2,000K; an intermediate CCT value of around 3,500K is exhibited shortly after sunrise or before sunset (when daylight is redder and softer compared to when the Sun is higher in the sky); and a color temperature of around 5,400K is exhibited around noontime. Color temperatures for various daylight sources are tabulated in FIG. 2. Low (or warm) color temperatures are consistent with reduced blue content, while higher (or cool) color temperatures are consistent with increased blue content.

Generally, a light that is dim and exhibits a low (warm) color temperature promotes restfulness (e.g., such as may be desirable in the evening and night before sleep), and a light that is bright and exhibits a high (cool) color temperature promotes alertness (such as may be desirable in the morning and during the day). A light having a very low intensity and a very low color temperature would least interfere with a person returning to sleep after being awakened in the middle of the night.

Color changing lights are known in the art. One example of a color changing light bulb is the Philips "Hue" bulb (Koninklijke Philips N. V., Eindhoven, the Netherlands). Such bulbs permit different colors, color temperatures, and/or intensities of light to be selected by a user via a computer or portable electronic device.

Despite the availability of color changing lights, it can be difficult for users to program lighting devices to obtain desired illumination conditions that take into account variations in natural light that may be attributable to multiple factors such as the season, latitude, time of day, and weather conditions.

It would be desirable to provide lighting devices and methods that address limitations of conventional lighting devices and methods.

SUMMARY

Embodiments disclosed herein relate to lighting devices and lighting systems arranged to receive or determine information indicative of geospatial or geographic location (and optionally additional information such as time, time zone, and/or date) and automatically adjust one or more light output parameters based at least in part on such information to operate one or more electrically activated emitters differently on different days of a year. A lighting device may include a memory and a processor to permit information to be stored and processed. At least one of a user input element, a signal receiver, and one or more sensors may be arranged to receive or provide a signal indicative of or permitting derivation of geospatial position. Examples of light output parameters that may be adjusted include color point of emissions, color temperature of emissions, spectral content of emissions, luminous flux of emissions, and operating time. Artificial light may be provided based on expected and/or sensed natural light conditions. In certain embodiments, a lighting device or lighting system may provide light of a brightness level and spectral content appropriate for the location (and preferably also appropriate for the time of day, day of week, and season). In certain embodiments, a lighting device or lighting system may further be adjusted to compensate for presence, absence, intensity, and/or color point of natural ambient light. In certain embodiments, a lighting device may determine a geospatial location, determine a date and/or time, and set a base schedule for operating the lighting device based on the geospatial location and the date/time. When the lighting device remains located at a given geospatial position, the base schedule in such embodiment may be reestablished on a periodic (e.g., daily, weekly, monthly, or seasonally) basis and automatically altered from day to day, from week to week, from month to month, or from season to season such that one or more electrically activated emitters are operated differently on different days of a year. Additionally, brightness and/or spectral content of the emissions of the lighting device may be further adjusted intraday based on sensed ambient conditions, sensed conditions of an illuminated space or surface, information indicative of weather conditions, and/or user inputs.

In one aspect, the disclosure relates to a lighting device comprising: at least one electrically activated emitter; at least one element selected from: (a) a user input element, (b) a signal receiver, and (c) at least one sensor, wherein the at least one element is arranged to receive or provide at least one signal indicative of or permitting derivation of geospatial position; and a driver module arranged to adjust operation of the at least one electrically activated emitter differently on different days of a year based on the at least one signal, wherein said adjustment alters at least one of the following: color point of emissions of the lighting device, color temperature of emissions of the lighting device, spectral content of emissions of the lighting device, luminous flux of emissions of the lighting device, and operating time of the lighting device. In certain embodiments, the at least one element is additionally arranged to receive or provide at least one signal indicative of or permitting derivation of any of date, time, and time zone. In certain embodiments, the at least one element includes any of a GPS receiver, a radio frequency receiver, a WiFi receiver, a Bluetooth receiver, a ZigBee receiver, a modulated light receiver, an infrared receiver, and an encoded power line signal receiver. A signal receiver may be arranged to receive at least one signal indicative of or permitting derivation of geospatial position. In certain embodiments, a signal receiver is configured to wirelessly receive at least one signal indicative of or permitting derivation of geospatial position from a portable digital device or personal computer. In certain embodiments, one, some, or all of at least one electrically activated emitter, a driver module, a user input element, a signal receiver, and at least one sensor may be arranged in, mounted on, or supported by a body structure of a lighting device.

In another aspect, the disclosure relates to a lighting system comprising: a plurality of lighting devices comprising a plurality of electrically activated emitters; at least one element selected from: (a) a user input element, (b) a signal receiver, and (c) at least one sensor, wherein the at least one element is arranged to receive or provide at least one signal indicative of or permitting derivation of geospatial position; and at least one driver module arranged to adjust operation of the plurality of electrically activated emitters differently on different days of a year based on the at least one signal, wherein said adjustment alters at least one of the following: color point of emissions of the lighting system, color temperature of emissions of the lighting system, spectral content of emissions of the lighting system, luminous flux of emissions of the lighting system, and operating time of the lighting system. In certain embodiments, the at least one element is additionally arranged to receive or provide at least one signal indicative of or permitting derivation of any of date, time, and time zone. The at least one element may be arranged remotely from each lighting device of the plurality of lighting devices. In certain embodiments, the first lighting device includes a signal transmitter arranged to transmit at least one signal indicative of or permitting derivation of geospatial position from the first lighting device to the second lighting device. In certain embodiments, the at least one element includes any of a GPS receiver, a radio frequency receiver, a WiFi receiver, a Bluetooth receiver, a ZigBee receiver, a modulated light receiver, an infrared receiver, and an encoded power line signal receiver. A signal receiver may be arranged to receive at least one signal indicative of or permitting derivation of geospatial position. In certain embodiments, a signal receiver is configured to wirelessly receive at least one signal indicative of or permitting derivation of geospatial position from a portable digital device or personal computer. In certain embodiments, a first driver module is associated with the first lighting device, a second driver module is associated with the second lighting device, the first driver module is arranged to drive a first group of solid state light emitters, and the second driver module is arranged to drive a second group of solid state light emitters.

In another aspect, the disclosure relates to a lighting system comprising: at least one element selected from: (a) a user input element, (b) a signal receiver, and (c) at least one sensor, wherein the at least one element is arranged to receive or provide at least one first signal indicative of or permitting derivation of geospatial position; a first lighting device comprising at least one first electrically activated emitter, a first wireless transmitter arranged to transmit at least one second signal derived from or including at least a portion of the at least one first signal, and a first driver module arranged to adjust operation of the at least one first electrically activated emitter differently on different days of a year based on the at least one first signal, wherein said adjustment of operation of the at least one first electrically activated emitter alters at least one of the following: color point of emissions of the first lighting device, color temperature of emissions of the first lighting device, spectral content of emissions of the first lighting device, luminous flux of emissions of the first lighting device, and operating time of the first lighting device; and a second lighting device comprising at least one second electrically activated emitter, a second receiver arranged to receive the at least one second signal from the first wireless transmitter, and a second driver module arranged to adjust operation of the at least one second electrically activated emitter differently on different days of a year based on the at least one second signal, wherein said adjustment of operation of the at least one second electrically activated emitter alters at least one of the following: color point of emissions of the second lighting device, color temperature of emissions of the second lighting device, spectral content of emissions of the second lighting device, luminous flux of emissions of the second lighting device, and operating time of the second lighting device. In certain embodiments, the at least one element is additionally arranged to receive or provide at least one signal indicative of or permitting derivation of any of date, time, and time zone. In certain embodiments, a signal receiver comprises any of a GPS receiver, a radio frequency receiver, a WiFi receiver, a Bluetooth receiver, a ZigBee receiver, a modulated light receiver, an infrared receiver, and an encoded power line signal receiver.

In another aspect, the present disclosure relates to a method for operating a lighting device including at least one electrically activated emitter, the method comprising: receiving by the lighting device, or providing to the lighting device, at least one signal indicative of or permitting derivation of geospatial position; establishing a base schedule configured to adjust operation of the at least one electrically activated emitter differently on different days of a year based on the at least one signal, wherein said adjustment of operation alters at least one of the following: color point of emissions of the lighting device, color temperature of emissions of the lighting device, spectral content of emissions of the lighting device, luminous flux of emissions of the lighting device, and operating time of the lighting device; and operating the at least one electrically activated emitter of the lighting device differently on different days of a year according to the base schedule. In certain embodiments, the method further comprises sensing any of an ambient light condition, a condition of an illuminated space or surface, and a weather condition; and responsive to said sensing, performing intraday adjustment of brightness and/or spectral content of light emissions of the lighting device to modify operation relative to operation of the lighting device specified in the base schedule. In certain embodiments, the method further comprises receiving by the lighting device, or providing to the lighting device, at least one signal indicative of or permitting derivation of at least one of date and time; and altering the base schedule based on the at least one of date and time. In certain embodiments, the at least one signal indicative of or permitting derivation of geospatial position is received by or provided by at least one element selected from: (a) a user input element, (b) a signal receiver, and (c) at least one sensor.

In another aspect, the present disclosure relates to a method comprising illuminating an object, a space, or an environment, utilizing a lighting device as described herein.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawings.

BRIEF DESCRIPTION OF THE DRAWINGS

The accompanying drawings incorporated in and forming a part of this specification illustrate several aspects of the disclosure, and together with the description serve to explain the principles of the disclosure.

FIG. 2 is a table providing color temperatures for various daylight sources.

FIG. 3 is a table identifying, for different times of day, ambient light, desired aptitude, and possible artificial light intensity levels and CCT values that may promote wellness when used with lighting devices and systems according to one embodiment of the disclosure.

FIG. 13A is a top perspective view of a solid state emitter package including four solid state emitter chips arranged over a substrate, covered with a hemispherical lens, and connected to electrical traces via wirebonds.

FIG. 13B is a bottom plan view of the solid state emitter package of FIG. 13A including four anodes and four cathodes arranged along opposing sides of a substrate, and a centrally arranged thermally conductive contact pad.

DETAILED DESCRIPTION

Figure 1:
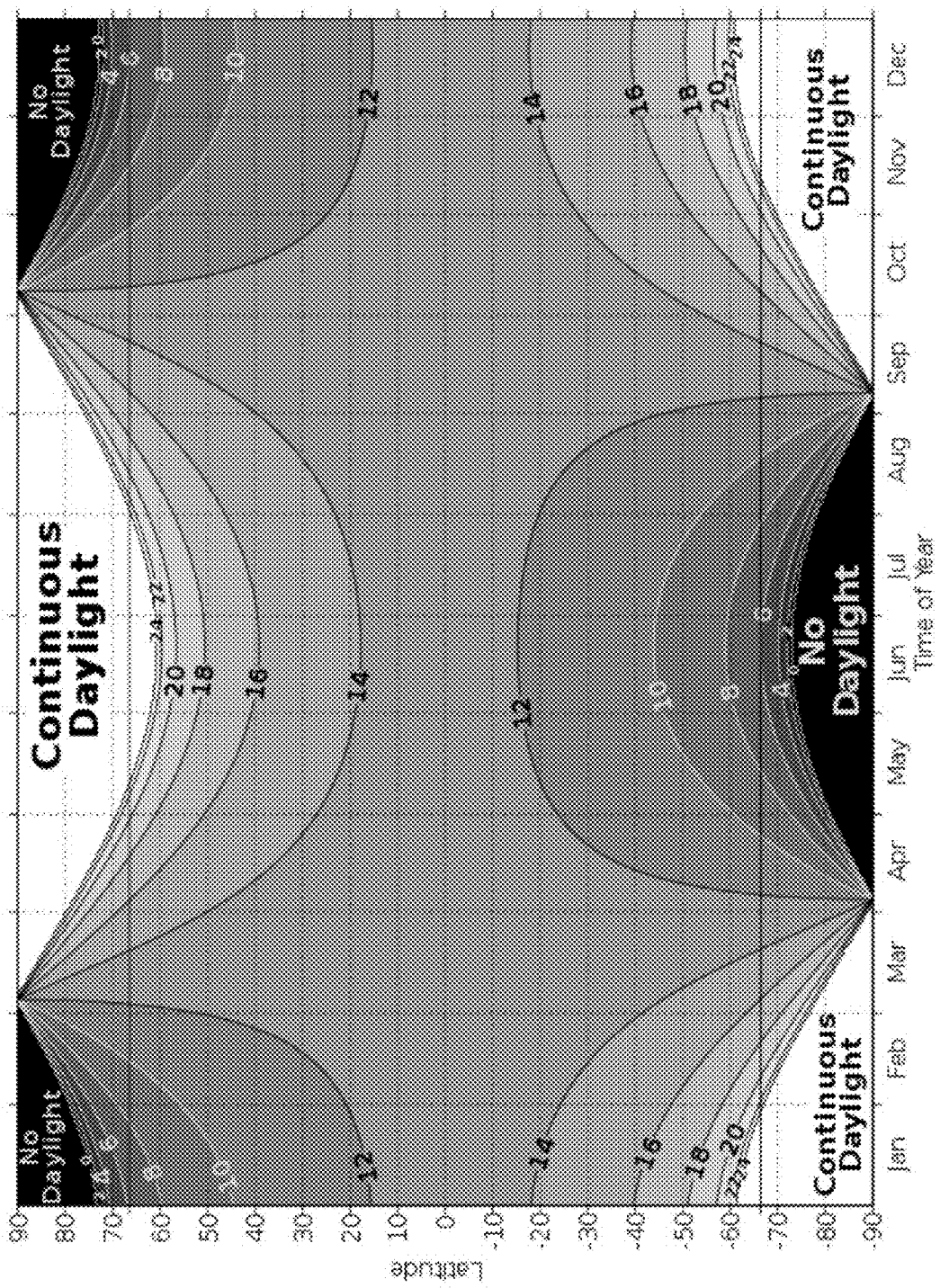
FIG. 1 is a contour plot of hours of daylight as a function of latitude and day of the year.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

Relative terms such as "below" or "above" or "upper" or "lower" or "horizontal" or "vertical" may be used herein to describe a relationship of one element, layer, or region to another element, layer, or region as illustrated in the figures. It will be understood that these terms and those discussed above are intended to encompass different orientations of the device in addition to the orientation depicted in the figures.

The terminology used herein is for the purpose of describing particular embodiments only and is not intended to be limiting of the disclosure. As used herein, the singular forms "a", "an", and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

The terms "electrically activated emitter" and "emitter" as used herein refers to any device capable of producing visible or near visible (e.g., from infrared to ultraviolet) wavelength radiation, including but not limited to, xenon lamps, mercury lamps, sodium lamps, incandescent lamps, and solid state emitters—including light emitting diodes (LEDs), organic light emitting diodes (OLEDs), and lasers.

The terms "solid state light emitter" or "solid state emitter" (which may be qualified as being "electrically activated") may include a LED, laser diode, OLED diode, and/or other semiconductor device which includes one or more semiconductor layers, which may include silicon, silicon carbide, gallium nitride and/or other semiconductor materials, a substrate which may include sapphire, silicon, silicon carbide and/or other microelectronic substrates, and one or more contact layers which may include metal and/or other conductive materials.

Solid state light emitting devices according to embodiments of the present disclosure may include, but are not limited to, III-V nitride based LED chips or laser chips fabricated on a silicon, silicon carbide, sapphire, or III-V nitride growth substrate, including (for example) devices manufactured and sold by Cree, Inc. of Durham, N.C. Solid state light emitters may be used individually or in groups to emit one or more beams to stimulate emissions of one or more lumiphoric materials (e.g., phosphors, scintillators, lumiphoric inks, quantum dots, day glow tapes, etc.) to generate light at one or more peak wavelength(s), or of at least one desired perceived color (including combinations of colors that may be perceived as white). Lumiphoric materials may be provided in the form of particles, films, or sheets.

Inclusion of lumiphoric (also called 'luminescent') materials in lighting devices as described herein may be accomplished by any suitable means, including: direct coating on solid state emitters, dispersal in encapsulant materials arranged to cover solid state emitters; coating on lumiphor support elements (e.g., by powder coating, inkjet printing, or the like); incorporation into diffusers or lenses; and the like.

The expressions "lighting device" and "light emitting device" as used herein are not limited, except that such elements are capable of emitting light. That is, a lighting device can be a device which illuminates an area or volume, e.g., a structure, a swimming pool or spa, a room, a warehouse, an indicator, a road, a parking lot, or a vehicle, signage, (e.g., road signs or a billboard), a ship, a toy, a mirror, a vessel, an electronic device, a boat, an aircraft, a stadium, a computer, a remote audio device, a remote video device, a cell phone, a tree, a window, a LCD display, a cave, a tunnel, a yard, a lamppost, or a device or array of devices that illuminate an enclosure, or a device that is used for edge or back-lighting (e.g., backlight poster, signage, LCD displays), light bulbs, bulb replacements (e.g., for replacing AC incandescent lights, low voltage lights, fluorescent lights, etc.), outdoor lighting, street lighting, security lighting, exterior residential lighting (wall mounts, post/column mounts), ceiling fixtures/wall sconces, under cabinet lighting, lamps (floor and/or table and/or desk), landscape lighting, track lighting, task lighting, specialty lighting, ceiling fan lighting, archival/art display lighting, high vibration/impact lighting-work lights, etc., mirrors/vanity lighting, or any other light emitting devices. An illuminated area may include at least one of the foregoing items. In certain embodiments, lighting devices as disclosed herein may be self-ballasted. In certain embodiments, a light emitting device may be embodied in a light bulb or a light fixture. In certain embodiments, a "lighting system" may include one lighting device or multiple lighting devices. In preferred embodiments, a "solid state lighting device" is devoid of any incandescent light emitting element.

Methods include illuminating an object, a space, or an environment, utilizing one or more lighting devices or lighting systems as disclosed herein. In certain embodiments, a lighting device as disclosed herein includes multiple LED components arranged in an array (e.g., a two-dimensional array).

Disclosed herein are lighting devices and lighting systems arranged to receive or determine information indicative of geospatial or geographic location (and optionally additional information such as time, time zone, and/or date) and automatically adjust one or more light output parameters based at least in part on such information to operate one or more electrically activated emitters differently on different days of a year. Light output parameters that may be adjusted according to certain embodiments include color point of emissions, color temperature of emissions, spectral content of emissions, luminous flux of emissions, and operating time. In certain embodiments, a lighting system may include multiple lighting devices. In certain embodiments, a lighting device may provide light of a brightness level and spectral content (e.g., color point and/or color temperature) appropriate for the location (and preferably also appropriate for the time of day, day of week, and season). In certain embodiments, a lighting device or lighting system may further be adjusted to compensate for presence, absence, intensity, and/or color point of natural ambient light.

In certain embodiments, adjustment of one or more light output parameters based at least in part on geospatial position on different days of year includes scheduled variation from week to week, variation from month to month, and/or variation from season to season. In certain embodiments, variation of light output parameters other than mere variation between weekday and weekend operating states, and variation of light output parameters other than semi-annual variation in daylight savings time, are contemplated. When the lighting device remains located at a given geospatial position, a base schedule for operation of emitters of the lighting device may be reestablished or automatically altered from day to day, from week to week, from month to month, or from season to season such that one or more electrically activated emitters are operated differently on different days of a year.

Determination of Geospatial Position, Date, and/or Time

In certain embodiments, a signal used by a lighting device or lighting system, and indicative of or permitting derivation of geospatial position, is provided by at least one of a user input element, a signal receiver, and one or more sensors. In certain embodiments, any one or more of a user input element, a signal receiver, and one or more sensors may be arranged in, arranged on, or supported by a body structure of a lighting device. In certain embodiments, any one or more of a user input element, a signal receiver, and one or more sensors may be physically separated from a body structure containing emitters of a lighting device, but may be arranged in communication with a driver module of a lighting device via wireless or wired communication.

Since a lighting device or lighting system as disclosed herein can automatically determine its geospatial position (and optionally, time zone and date), in certain embodiments, a lighting device can automatically adjust its light output parameters in a manner suitable for the geospatial position, and preferably also in a manner suitable for the current date and time.

In certain embodiments, a lighting device or lighting system includes, or is arranged in at least intermittent communication with, a global positioning system (GPS) receiver that is arranged to receive global positioning coordinates (e.g., latitude and/or longitude coordinates) or other information as indicative of geospatial position. A GPS receiver may also provide accurate time and date information useable by the lighting device or lighting system. In certain embodiments, a GPS receiver of a lighting device (e.g., an outdoor floodlight) is positioned in direct line-of-sight communication with a GPS satellite. In certain embodiments, a GPS receiver is positioned remotely from a lighting device but is arranged to communicate a received GPS signal to the lighting device via either wired or wireless transmission.

In certain embodiments, a lighting device may be arranged to communicate with an electronic device that includes location sensing capability, and the lighting device may obtain location information (and/or date and time information) from the electronic device. In certain embodiments, such an electronic device may embody a smartphone or other portable digital device having integrated GPS, WiFi, and/or cellular communication capabilities that provide the portable digital device with location information, and such location information may be communicated to a lighting device by either wireless or wired means (e.g., temporarily via a cord and an appropriate communication port such as described hereinafter). In certain embodiments, a user may download software (such as may be embodied in a software application) that facilitates communication between an electronic device with communication capability and a lighting device as disclosed herein.

In certain embodiments, a lighting device or lighting system includes, or is arranged in at least intermittent communication with, a signal receiver arranged to receive a signal and extract at least one Internet Protocol (IP) address from one or more proximate IP-enabled servers, routers, or other devices in order to at least approximately determine geospatial position and/or time and date information. Such signal may be received via wireless (e.g., radio frequency or modulated light) or wired means. In certain embodiments, a lighting device includes a radio frequency receiver. In certain embodiments, a signal may be received via WiFi, ZigBee, Bluetooth, infrared, modulated light, audio tone, Ethernet, or another wired or wireless connection. In the same manner that webpages determine the geographic area of a user by checking which ISP is connected to the computer, a lighting device or lighting system may be arranged to receive a signal with IP address information and utilize such information to determine at least approximate geospatial position. In certain embodiments, a signal receiver may also receive time and date information from one or more proximate IP-enabled servers, routers, or other devices.

In certain embodiments, a lighting device or lighting system may receive information indicative of, or permitting derivation of, geospatial position, as well as date and/or time information, by reception of broadcast radio and/or broadcast television signals. In certain embodiments, a lighting device may include a broadcast radio and/or a broadcast television signal receiver, and may include a demultiplexer or other signal decoder arranged to extract position-identifying information, date information, and/or time information encoded in the broadcast radio or broadcast television signal. In certain embodiments, a lighting device includes a FM receiver and may be arranged to receive signals including digital information encoded according to the Radio Data System (RDS) protocol or the Radio Broadcast Data System (RBDS) protocol, wherein encoded information may include clock time, date, program identification (identifying the station), and the like. Signals according to other radio or television protocols may be used. In certain embodiments, a lighting device may receive multiple broadcast television (of analog and/or digital varieties) and/or broadcast radio signals (of analog and/or digital varieties) and perform triangulation based on relative signal strength to determine geospatial location.

In certain embodiments, a lighting device or lighting system may receive information indicative of, or permitting derivation of, geospatial position, as well as date and/or time information, via signals encoded on a power line. In certain embodiments, a lighting device may include a demultiplexer or other signal decoder arranged to extract position-identifying information, date information, and/or time information encoded in a power signal (e.g., alternating current power signal) supplied to the lighting device.

In certain embodiments, a lighting device or lighting system includes, or is arranged in at least intermittent communication with, a light sensor arranged to receive ambient light (e.g., daylight) in order to permit determination of geospatial position. In certain embodiments, a lighting device may receive and store an ambient light signal, and analyze such information gathered over time to determine (at least approximate) geospatial position. In certain embodiments, an ambient light (or daylight) sensor may enable calculation or estimation of geospatial position based on when natural light first appears, duration of presence of natural light, and how the light varies over time (e.g., both intraday and in longer time scales such as from day to day and from month to month). In certain embodiments, determination of geospatial position from sensed light may exclude fast changes in light level such as those caused by moving shadows or by artificial lights that are activated or deactivated in an instantaneous manner. In certain embodiments, a light sensor may examine the spectral content of received light to determine its "naturalness" (e.g., whether the received light embodies or includes spectral content consistent with daylight, or whether the received light is representative of artificial light). In certain embodiments, determination of geospatial position from information received by a light sensor may utilize one or more items of additional information, such as date, time, time zone, postal code, country code, telephone area code, IP address of a proximate device, or a similar parameter. Such additional information may be gathered by one or more sensors, user input elements, and/or signal receivers.

In certain embodiments, determination of geospatial position may be further aided with an altitude and/or pressure sensor, since altitude can affect light conditions.

In certain embodiments, a lighting device or lighting system is arranged to receive from a user input element a signal indicative of, or permitting derivation of, geospatial position. In certain embodiments, a user input element may be integrated with a lighting device; alternatively, a user input element may be separable from a lighting device and communicate signals via wired or wireless communication.

In certain embodiments, a user input element may include or embody a remote controller arranged to communicate with a lighting device via an infrared, radio frequency, or other wireless signal type. In certain embodiments, a user input element may include or embody a general purpose portable digital device such as a smartphone, tablet computer, personal computer, laptop, or the like, arranged to operate software and permitting wired or wireless communication with a lighting device (e.g., via Bluetooth, ZigBee, WiFi, or other signal types). In certain embodiments, a lighting device may receive from a user input element geospatial position or information indicative thereof, optionally in conjunction with lighting device configuration and/or operating information that may be entered or modified by a user. In certain embodiments, a lighting device may receive from a user input element automatically obtained information or user-entered information such as a GPS signal, an IP address, a time zone, a telephone area code, a postal code, a country code or name, a state or province code or name, a latitude, a longitude, or the like, to permit a lighting device to determine or derive geospatial position.

In certain embodiments, a user input element may be arranged to communicate with a lighting device via wired communication. In certain embodiments, a body structure associated with a lighting device may include one or more buttons, sliders, dials, touchpads, or the like to receive input signals from a user. In certain embodiments, a lighting device may include a wired communication port (e.g., USB, Ethernet, Firewire, or the like) arranged to receive a cord for attachment to an input device such as a smartphone, tablet computer, personal computer, laptop, or the like.

Utilization of Sensors

In certain embodiments, any one or more of various types of sensors may be included in, or in at least intermittent communication with, a lighting device or lighting system. In certain embodiments, a lighting device may have associated therewith at least one of an ambient light sensor (e.g., arranged to sense intensity and/or spectral content of ambient light), an occupancy sensor (e.g., arranged to detect a condition indicating that an illuminated space is or is not occupied by at least one person), an image sensor (e.g., still or video), a sound sensor (e.g., microphone), and a temperature sensor (e.g., thermistor). If multiple sensors are provided, they may be used to sense the same or different environmental conditions. If multiple sensors are used to sense the same environmental conditions, different types of sensors may be used. In certain embodiments, one or more sensors may be arranged in a sensor module arranged in or on a lighting device. In certain embodiments, one or more sensors may be arranged remotely from a lighting device but in communication with the lighting device via wired or wireless signal transmission.

In certain embodiments, one or more sensors may be integrated with or arranged in communication with a personal computer, a portable digital device (e.g., a smartphone), or a remote controller, and signals derived from such sensor(s) may be communicated to a lighting device to be used by the lighting device. Communication between a lighting device and one or more remotely arranged sensors (e.g., associated with a smartphone) may be updated substantially continuously, updated periodically according to a predefined or user-defined schedule, or may be updated in response to a user command.

As noted previously, one or more sensors may be used in determining geospatial position and/or date or time, and a base schedule for operating a lighting device may be established based on geospatial location and the date/time. Such base schedule may be reestablished on a periodic basis and automatically altered from day to day, from week to week, from month to month, or from season to season so that one or more electrically activated emitters are operated differently on different days of a year. Additionally, one or more sensors may be used to sense ambient conditions and/or conditions of an illuminated space or surface, and such sensed conditions may be used to facilitate intraday adjustment of brightness and/or spectral content of the emissions of the lighting device relative to operation according to a base schedule previously established and in effect for that day.

If provided, an ambient light sensor may take on different configurations. In a first configuration, an ambient light sensor may be separate from emitters of a lighting device and associated with control circuitry to facilitate monitoring of the ambient light characteristic. An ambient light sensor may be a specially configured light sensor or another LED that is configured to generate a current indicative of the ambient light characteristic in response to being exposed to the ambient light. If a plurality of LEDs are driven with pulses of current, then an ambient light characteristic may be monitored between any two pulses of current. Alternatively, one or more main LEDs may be used by the control circuitry to monitor the ambient light characteristic, such as by monitoring ambient light between any two pulses of LED drive current.

If provided, an occupancy sensor may be used to determine a condition indicating presence or absence of at least one person in an illuminated space. In certain embodiments, detection of a condition indicating that an illuminated space is not occupied may be used to terminate or alter operation of a lighting device.

The intensity and spectral output of the light emitted by electrically activated emitters (e.g., LEDs) may be affected by temperature. In certain embodiments, a temperature sensor associated with a lighting device may be used to sense temperature of one or more emitters, and current to the emitters may be controlled based on the sensed temperature in an effort to compensate for temperature effects.

In certain embodiments, output of an ambient light sensor and/or an image sensor may be used to promote efficient operation of a lighting device while maintaining a desired threshold of color rendering index (CRI) of light in or on an illuminated region or surface. For example, a lighting device may include a high CRI emitter having a relatively low efficiency, in combination with a lower CRI emitter having a relatively high efficiency. If ambient light of sufficiently high CRI is detected in sufficient amount in or on a region or surface, then it may be possible to drive a high efficiency but low CRI emitter with increased current (and reduced current to the high CRI but low efficiency emitter) to achieve desired illumination with acceptably high CRI, thereby promoting efficiency operation.

Adjustment of Light Output Parameters

As noted previously, one or more light output parameters of a lighting device may be adjusted at least in part based on information indicative of geospatial or geographic location, and optionally additional information such as time, time zone, and/or date. Examples of light output parameters that may be adjusted include color point of emissions, color temperature of emissions, spectral content of emissions, intensity or luminous flux of emissions, and operating time. In certain embodiments, a lighting device includes multiple independently controllable emitters (or groups of emitters) having different color points. By altering proportion of current to different emitters having different color points, a lighting device may be adjusted to produce aggregate emissions of a range of different colors and/or color temperatures.

In certain embodiments, a base schedule for a lighting device may be configured to promote wellness by providing output that promotes alertness in morning to afternoon hours, that promotes alertness and relaxation in mid-afternoon to evening hours, that promotes relaxation and sleepiness in late evening to bedtime hours, and that does not interfere with sleeping and/or does not interfere with night vision from midnight to dawn hours. FIG. 3 is a table identifying, for different times of day, ambient light, desired aptitude, and possible artificial light intensity levels and CCT values that may promote wellness when used with lighting devices and systems according to one embodiment of the disclosure. It is known that exposure to light of high intensity and high color temperature promotes alertness; accordingly, a lighting device may output high intensity emissions of a color temperature in excess of 6000K from dawn to mid-morning to promote wakefulness. A somewhat lower color temperature (in a range of from 3500K to 5000K, or from 4000K to 5000K) with sustained high intensity may be output from mid-day through the afternoon to promote alertness. Progressing into the evening, a lighting device may output emissions of lower intensity and a lower (warmer) color temperature (e.g., from 2000K to 3000K) with reduced blue spectral content to avoid melatonin suppression, and thereby promote relaxation prior to bedtime. In the middle of the night to dawn, a lighting device may output emissions of very low intensity and with a very low color temperature (e.g., below 1500K) to avoid interference with sleep and avoid loss of night vision in case a person's sleep is interrupted. The preceding variation in intensity and color temperature of a lighting device may be controlled by a base schedule.

In certain embodiments, a base schedule for operation of a lighting device or lighting system may be altered or programmed by a user, such as by using one or more user input elements. For example, a user that is required to work during evening hours and to sleep during daytime hours may program a lighting device to output emissions having a high intensity and a high color temperature during evening hours to promote alertness while the user is working, with a transition to lower intensity and lower color temperature to a time allotted for the user to sleep. In certain embodiments, a user may simply shift a base schedule by a selected number of hours, based on a selected wake-up time, a selected time to bed, and/or a selected period for work or other activity requiring alertness.

In certain embodiments, a lighting device may be configured to accept user inputs to initiate actions, to accept user inputs to adjust response of a lighting device to time of day, and/or accept user inputs to adjust response to an ambient lighting condition.

In certain embodiments, color temperature of a lighting device may be synchronized to local variation of ambient light color temperature with respect to geographic location or geospatial position, time of day, and day of year. For example, a lighting device may emulate natural outdoor light levels and color spectral content when it is dawn, dusk, and midday, with such emulation matched to the geospatial position or geographic location of the lighting device.

In other embodiments, a base schedule of a lighting device may be modified, or an alternate base schedule may be selected, to mitigate symptoms of seasonal affective disorder by providing increased intensity and/or color temperature of light at at least certain times of day. In certain embodiments, a lighting device may detect that it is located in a geographic location or geospatial position consistent with increased incidence of seasonal affective disorder, and either prompt a user to select, or automatically initiate operation of, a base schedule suitable to mitigate symptoms of seasonal affective disorder.

Communication with and Between Lighting Devices

In certain embodiments, a lighting device or lighting system includes at least one signal transmitter and/or receiver, such as may be optionally embodied in at least one transceiver. In certain embodiments, a transmitter and/or receiver may be arranged to transmit and/or receive radio frequency signals.

In certain embodiments, a lighting device may communicate with one or more other lighting devices such that the devices can share information. This may be useful when a first lighting device lacks a clear connection to a desired GPS signal, user input, other external signal, or other sensory input, but when a second lighting device has a clear connection. In such an instance, the second lighting device may receive a signal from a GPS satellite, a user input device, a RF receiver, or one or more sensors, and the second lighting device may transmit the received information to the first lighting device to permit the first lighting device to take appropriate action (e.g., update geospatial position, update time/date, adjust base schedule, and/or adjust operating state). In certain embodiments, lighting devices may communicate with one another via signals encoded on a power line. Thus, via either wired or wireless communication, one lighting device may propagate information to one or more other lighting devices, and the shared information may be used to automatically adjust one or more light output parameters to cause the lighting devices to operate one or more electrically activated emitters differently on different days of a year.

Features of Exemplary Lighting Devices, Systems, and Methods

Additional features of lighting devices, lighting systems, and related methods according to the present disclosure may be understood with reference to FIGS. 4-17.

Figure 4:
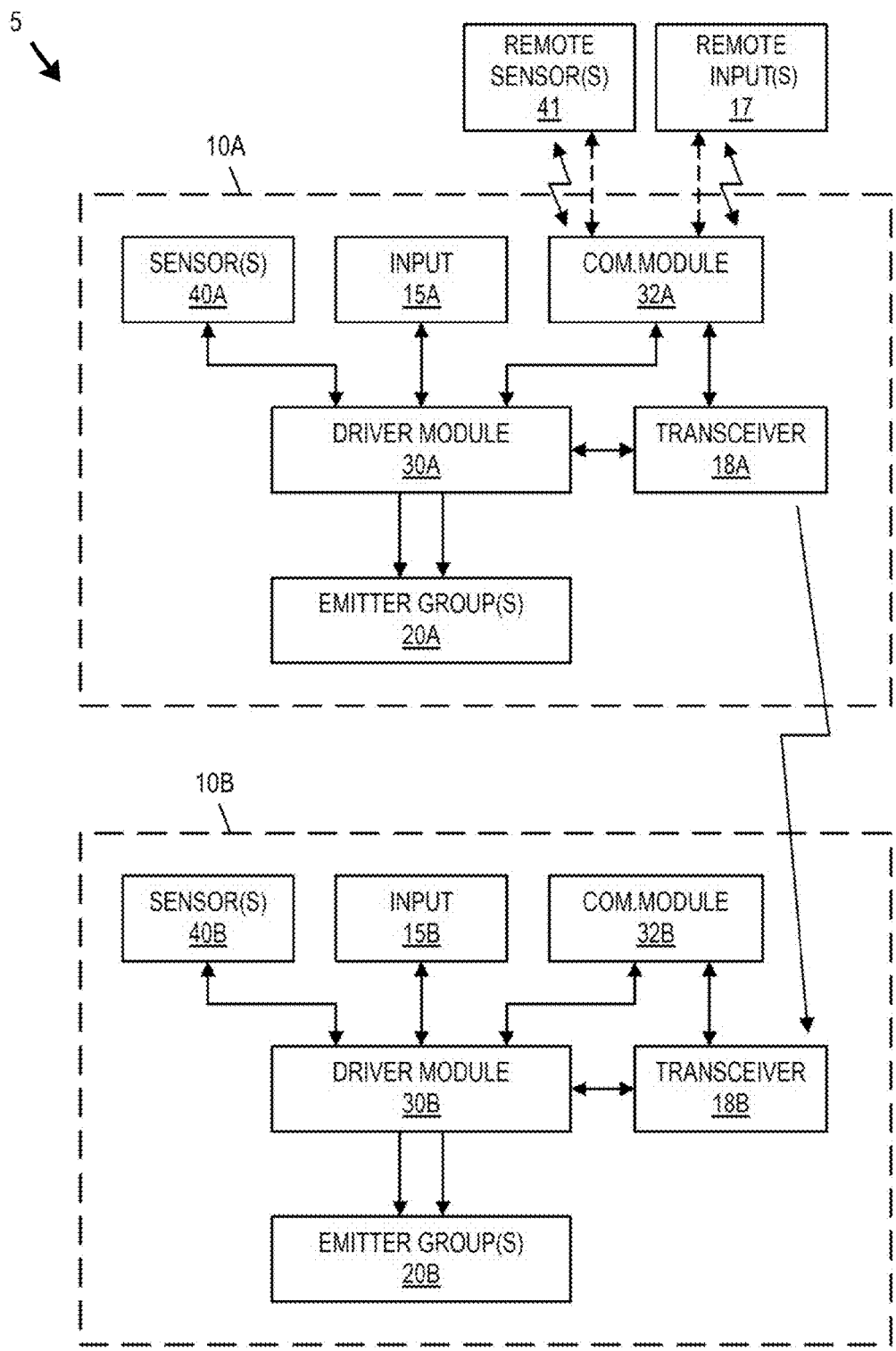
FIG. 4 is a simplified schematic showing interconnections within and between two lighting devices of a lighting system according to one embodiment of the disclosure.

FIG. 4 is a simplified schematic showing interconnections within and between two lighting devices 10A, 10B of a lighting system 5 according to one embodiment. The first lighting device 10A includes a driver module 30A, one or more sensors 40A, a user input element 15A, a communication module 32A, a transceiver 18A, and one or more emitter groups 20A. The second lighting device 10B includes a driver module 30B, one or more sensors 40B, a user input element 15B, a communication module 32B, a transceiver 18B, and one or more emitter groups 20B. One or more remote sensors 41 and one or more remote input elements 17 may be arranged in at least intermittent communication with one or more of the lighting devices 10A, 10B.

Within each lighting device 10A, 10B, the respective emitter groups 20A, 20B preferably include multiple electrically activated emitters, and more preferably include multiple solid state emitters arranged to output different color points. By altering proportion of current to different emitters having different color points, a lighting device may be adjusted to produce aggregate emissions of a range of different colors and/or color temperatures. The driver module 30A, 30B of each lighting device 10A, 10B is arranged to drive emitters of emitter group(s) 20A, 20B of the respective lighting device 10A, 10B. In certain embodiments, the driver module 30A, 30B provides the primary intelligence for the respective lighting device 10A, 10B and is capable of driving emitters of the emitter groups 20A, 20B, in a desired fashion. Each driver module 30A, 30B may be embodied in a single, integrated module or divided into two or more sub-modules as desired.

When a driver module 30A, 30B provides the primary intelligence for its respective lighting device 10A, 10B, the communication module 32A, 32B may act as an intelligent communication interface to facilitate communications between the driver module 30A, 30B and one or more remote sensors 41 and/or one or more remote input elements 17. The remote sensor(s) 41 and/or remote input element(s) 17 may be configured to communicate with one or more lighting devices 10A, 10B in a wired or wireless fashion.

Alternatively, each driver module 30A, 30B may be primarily configured to drive emitters of its respective emitter group(s) 20A, 20B based on instructions from the respective communication module 32A, 32B. In such an embodiment, the primary intelligence of each lighting device 10A, 10B may be provided in the respective communication module 32A, 32B, which may embody an overall control module with wired or wireless communication capability. Each communication module 32A, 32B may include or have associated therewith at least one transceiver 18A, 18B, wherein each transceiver 18A, 18B may be optionally replaced with separate transmitter and receiver components. Each communication module 32A, 32B may facilitate the sharing of intelligence and signals among the various lighting devices 10A, 10B and other entities.

In certain embodiments, each communication module 32A, 32B may be implemented on a printed circuit board (PCB) that is separate from a circuit board associated with the respective driver module 30A, 30B. In certain embodiments, communication between a communication module 32A, 32B and a corresponding drive module 30A, 30B may be made via cables according to a desired communication interface, optionally including one or more interface plugs. In certain embodiments, each lighting device 10A, 10B may include a body structure, and the driver module 30A, 30B, communication module 32A, 32B, and emitter group(s) 20A, 20B of the respective lighting device 10A, 10B may be arranged in or on the body structure.

Figure 5:
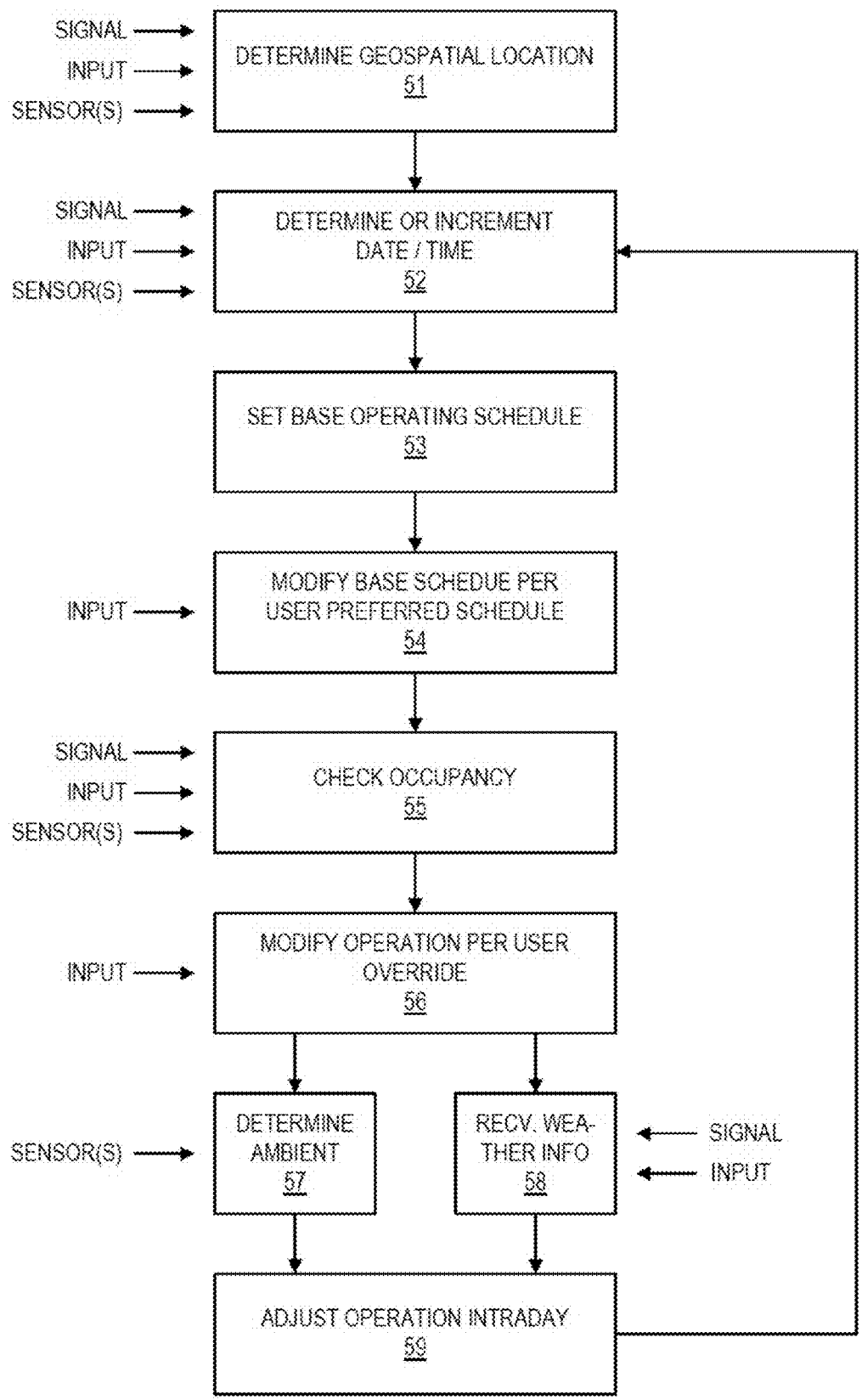
FIG. 5 is a diagram that illustrates functional steps for operating a lighting device or lighting system according to one embodiment of the disclosure.

FIG. 5 is a diagram that illustrates functional steps for operating a lighting device or lighting system as disclosed herein according to certain embodiments. A first step 51 includes determination by a light device of its geospatial location. Such determination may be made utilizing a received (e.g., data) signal, an input signal, and/or one or more sensors. A second step 52 includes determining or incrementing date and/or time information stored by the lighting device or lighting system. Such determination may be made utilizing a received (e.g., data) signal, an input signal, and/or one or more sensors. A third step 53 includes setting a base schedule for operating the lighting device based on the geospatial location and the date/time. In certain embodiments, the base schedule in such embodiment may be reestablished on a periodic (e.g., daily, weekly, monthly, or seasonally) basis and automatically altered from day to day, from week to week, from month to month, or from season to season such that one or more emitters are operated differently on different days of a year.

Continuing to refer to FIG. 5, a fourth step 54 for operating a lighting device or lighting system may involve checking for modification of, and modifying, a base schedule to take into account operational parameters or constraints preferred by a user. Such modification may be made utilizing an input signal received from one or more input elements. Modification of a schedule by a user may include, for example, temporal shifts in activation or deactivation of a lighting device, scheduled shifts in desired color point at different times of day, scheduled limits for minimum or maximum intensity of emissions, and so on. In certain embodiments, the fourth step 54 includes input by a user of preferences for modifying scheduled operation of a lighting device, and storage in memory of the modified schedule—either by overwriting a previously established base schedule, or by storing a modified operating schedule separately from a previously established base schedule while maintaining a previously established base schedule. A fifth step 55 includes checking for occupancy in a space or area to be illuminated to determine if illumination is required. Checking for occupancy may utilize a received (e.g., data) signal, an input signal, and/or one or more sensors. In certain embodiments, if it is determined that a space or area to be illuminated is not occupied, then a lighting device may be temporarily deactivated, operated at a reduced intensity, or operated at a modified color point or color temperature. A sixth step 56 includes checking for temporary modification of a lighting device according to a user override signal, such as may be received via one or more user input elements. Examples of possible override signals may include instantaneously activating or deactivating a lighting device, instantaneously setting minimum or maximum intensity limits, instantaneously changing color point or color temperature, and so on. In certain embodiments, override signals may be implemented in a substantially instantaneous manner and may be maintained for a predetermined or user-determined time period that may be tracked by a clock or timer associated with a lighting device or associated with a user input element. In certain embodiments, the sixth step 56 differs from the fourth step 54 in that the sixth step 56 may be primarily directed to instantaneous and temporary modifications to a predefined (e.g., base) schedule for operating a lighting device or system, whereas the fourth step 54 may be primarily directed to longer-term modifications to a predefined operating schedule for operating the lighting device or system.

With continued reference to FIG. 5, a seventh step 57 for operating a lighting device or lighting system may include determining an ambient condition (whether associated with an illuminated space or area, or associated with an environment outside the illuminated space or area). Such determination may be performed utilizing one or more sensors (e.g., light sensors, image sensors, temperature sensors, or the like). In certain embodiments, such determination may be made utilizing a signal receiver arranged to receive a signal indicative of at least one ambient condition from an electronic device such as a smartphone, tablet computer, or other portable digital device. An eighth step 58 may include receiving information of weather conditions or other ambient conditions. Such information may be received via one or more signal receivers and/or user input elements. For example, weather information may be received via wired or wireless transmission from one or more personal digital devices, Internet websites, radio stations, television stations, or weather stations. Based on the seventh and/or eighth steps 57, 58, operation of a lighting device or lighting system may be adjusted intraday according to a ninth step 59. Examples of light output parameters that may be adjusted include color point of emissions, color temperature of emissions, spectral content of emissions, luminous flux of emissions, and operating time. Following performance of the ninth step 59, operation may continue by returning to any desired preceding step 51-58. In certain embodiments, operation is continued by returning to the second step 52 to increment the date or time. In certain embodiments, operation may at least periodically continue by returning to the first step 51 to check whether geospatial location has changed. In certain embodiments, one or more of the preceding steps 51-59 may be omitted or modified as desired, or additional steps may be performed.

Various types of lighting devices and systems are contemplated according to embodiments of the disclosure. Certain embodiments may be directed to lighting fixtures (including in-ceiling, recessed, pendant, and surface mount varieties), light bulbs, street lamps, indoor lamps, outdoor lamps, desk lamps, floor-standing lamps, and so on.

Figure 6A:
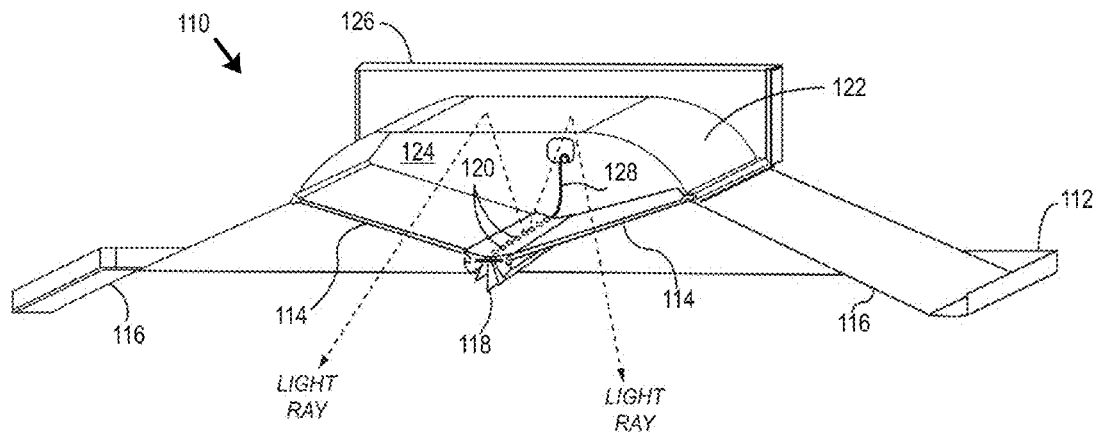
FIG. 6A is a cross-sectional perspective view of a troffer-based lighting fixture according to one embodiment of the disclosure, illustrating how light emanates from emitters of the light fixture and is reflected to be transmitted through lenses of the lighting fixture.

FIG. 6A provides a cross-sectional perspective view of a lighting device in the form of a troffer-based lighting fixture 110 according to one embodiment of the disclosure. This particular lighting fixture is substantially similar to the CR and CS series of troffer-type lighting fixtures that are manufactured by Cree, Inc. of Durham, N.C. While the disclosed lighting fixture 110 employs an indirect lighting configuration wherein light is initially emitted upward from a light source and then reflected downward, lighting devices including direct lighting configurations are within the scope of the present disclosure. In addition to troffer-type lighting fixtures, concepts disclosed herein may be utilized in recessed lighting configurations, wall mount lighting configurations, outdoor lighting configurations, and the like. Further, the functionality and control techniques described below may be used to control different types of lighting devices, as well as different groups of the same or different types of lighting devices at the same time.

In general, troffer-type lighting fixtures, such as the lighting fixture 110, are designed to mount in, on, or from a ceiling, such as a drop ceiling (not shown) of a commercial, educational, or governmental facility. As illustrated in FIG. 6A, the lighting fixture 110 includes a square or rectangular outer frame 112. A central portion of the lighting fixture 110 includes two rectangular lenses 14, which are generally transparent, translucent, or opaque. Reflectors 116 extend from the outer frame 112 to outer edges of the lenses 114. The lenses 114 effectively extend between the innermost portions of the reflectors 116 to an elongated heatsink 118, which abuts inside edges of the lenses 114. An upwardly facing portion of the heatsink 118 provides a mounting structure for an LED array 120, which supports one or more rows of LEDs oriented to primarily emit light upwards toward a concave cover 122. The volume bounded by the cover 122, the lenses 114, and the heatsink 118 provides a mixing chamber 124. Light emanates upward from the LED array 120 toward the cover 122 and is reflected downward through the respective lenses 114, as illustrated in FIG. 6A. Some light rays will reflect multiple times within the mixing chamber 124 and effectively mix with other light rays, such that a desirably uniform light is emitted through the respective lenses 114.

Figure 6B:
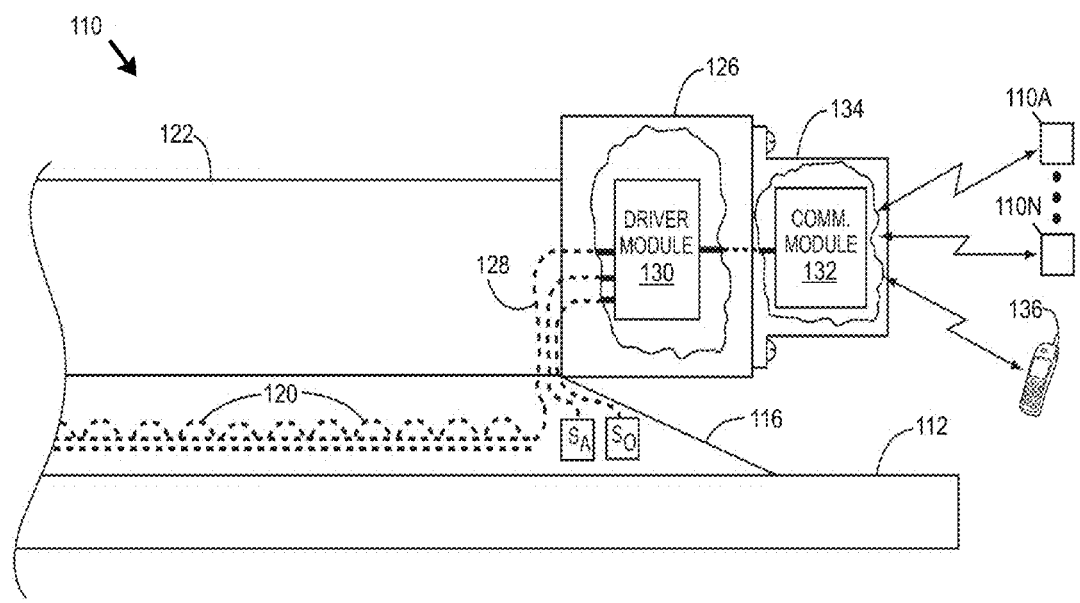
FIG. 6B illustrates a driver module provided in an electronics housing of the lighting fixture of FIG. 6A and a communication module in an associated housing coupled to the exterior of the electronics housing according to one embodiment of the disclosure.

As shown in FIG. 6B, an electronics housing 126 may be mounted at one end of the lighting fixture 110 to house some or all electronics used to power and control the LED array 120. These electronics are coupled to the LED array 120 through appropriate cabling 128. The electronics provided in the electronics housing 126 may be divided into a driver module 130 and a communication module 132. The communication module 132 may communicate with one or more external devices such as a user input element 136 (which may optionally be embodied in a smartphone, tablet computer, a wireless remote controller, or the like), and one or more other lighting devices (e.g., fixtures) 110A-110N. The communication module 132 may be arranged in a secondary housing 134 that is mechanically coupleable to the electronics housing 126 to promote modularity, upgradeability, and/or serviceability. The lighting fixture 110 further includes a sensor module including one or more sensors, such as occupancy sensors $S_O$, ambient light sensors $S_A$, temperature sensors, sound sensors (microphones), image (still or video) sensors, and the like. In certain embodiments, one or more sensors may be arranged external to or remote from the lighting device 110. Additionally, one or more wired user input elements (not shown) may optionally be arranged in communication with the communication module 132 and/or the driver module 130.

Figure 7:
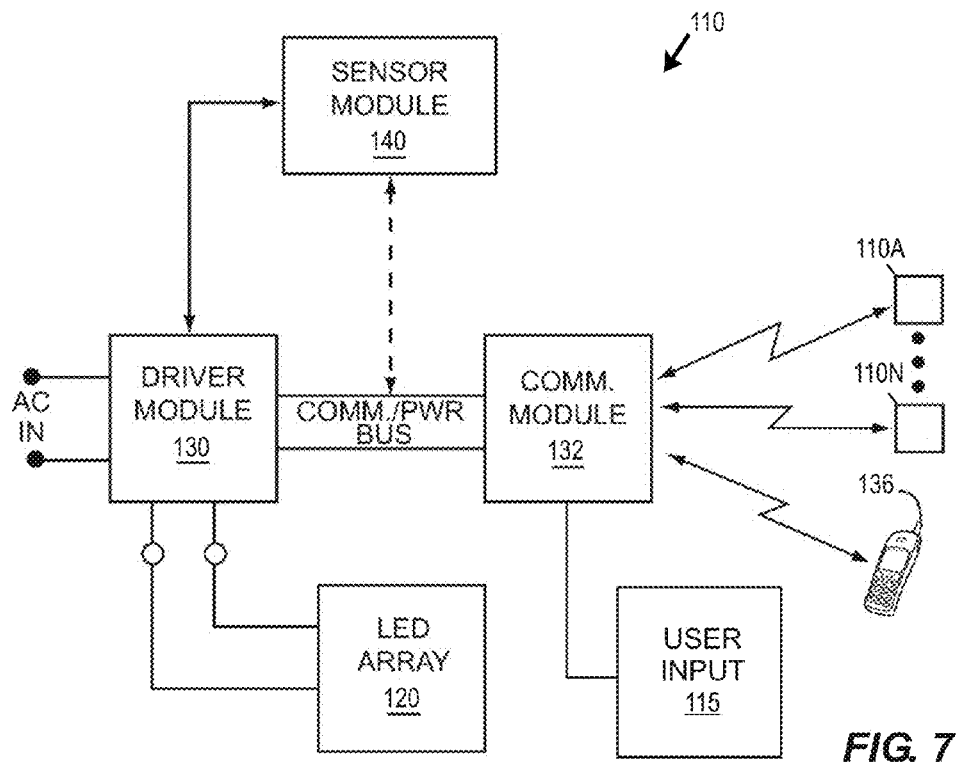
FIG. 7 is a block diagram of a lighting system according to one embodiment of the disclosure.

Turning now to FIG. 7, an electrical block diagram for a lighting fixture 110 is provided. In certain embodiments, the driver module 130, communication module 132, and LED array 120 may be connected to form core electronics of the lighting fixture 110, and the communication module 132 may be configured to bidirectionally communicate with other lighting devices 110A-110N as well as one or more user input elements 115, 136 via wired or wireless techniques. In certain embodiments, a standard communication interface and a first (or standard) protocol may be used between the driver module 130 and the communication module 132, thereby permitting different driver modules 130 to communicate with and be controlled by different communication modules 132. The term "standard protocol" may be defined to mean any type of known or future developed, proprietary, or industry-standardized protocol.

In the illustrated embodiment, the driver module 130 and the communication module 132 are coupled via communication and power buses, which may be separate or integrated with one another. A communication bus allows the communication module 132 to receive information from the driver module 130 as well as control the driver module 130. An exemplary communication bus is the well-known inter-integrated circuitry (I2C) bus, which is a serial bus and is typically implemented with a two-wire interface employing data and clock lines. Other available buses include: serial peripheral interface (SPI) bus, Dallas Semiconductor Corporation's 1-Wire serial bus, universal serial bus (USB), RS-232, Microchip Technology Incorporated's UNI/O®, and the like. In certain embodiments, one or more user input elements 115, 136 may be coupled to the communication bus or the driver module 130.

The driver module 130 may be configured to collect data from a sensor module 140, which may include an ambient light sensor $S_A$, an occupancy sensor $S_O$, a GPS sensor, and/or any other suitable sensors disclosed herein. The driver module 130 is further arranged to drive LEDs of the LED array 120. Data collected from the sensor module 140 $S_O$ as well as any other operational parameters of the driver module 130 may be shared with the communication module 132. As such, the communication module 132 may collect data about the configuration or operation of the driver module 130 and any information made available to the driver module 130 by the LED array 120 and/or the sensor module 140. The collected data may be used by the communication module 132 to control operation of the driver module 130, may be shared with other lighting devices 110A-110N or user input elements, or may be processed to generate data or instructions that are sent to other lighting devices 110A-110N. In certain embodiments, the sensor module 140 may be coupled directly to the communications bus instead of directly to the driver module 130, such that sensory information from the sensor module 140 may be provided to the driver module 130 or the communication module 132 via the communications bus.

In certain embodiments, the communication module 132 may be controlled in whole or in part by a remotely located entity, such as a user input element 136 or another lighting device 110A-110N. The communication module 132 may process sensor data and/or instructions provided by other lighting device 110A-110N or a remotely located user input element 115, 136, and then provide instructions over the communication bus to the driver module 130. The communication module 132 may therefore facilitate the sharing of system information with the driver module 130, which may use internal logic to determine what action(s) to take. The driver module 130 may respond by controlling the drive current or voltages provided to the LED array 120 as appropriate.

In certain embodiments, one aspect of a standard communication interface is the definition of a standard power delivery system. The power bus may be set to a desired (e.g., low) voltage level, such as 5 volts, 12 volts, 24 volts, or the like. The driver module 130 may be configured to process an AC input signal to provide the defined low voltage level over power bus. The communication module 132 and/or auxiliary devices, such as the sensor module 140, may be designed in anticipation of the desired low voltage level being provided over the power bus by the driver module 130, without concern for connecting to an AC power source or performing AC to DC conversion for powering the electronics of the communication module 132 or the sensor module 140.

Figure 8:
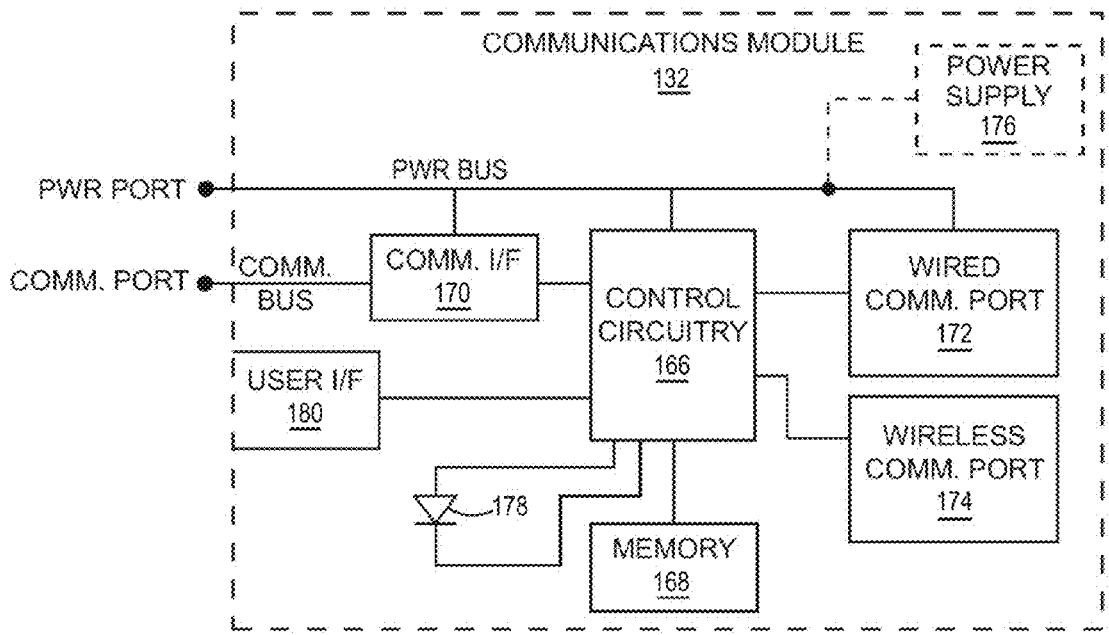
FIG. 8 is a block diagram of a communication module according to one embodiment of the disclosure.

Turning to FIG. 8, a block diagram of a communication module 132 according to one embodiment is provided. The communication module 132 includes control circuitry 166 and associated memory 168, which contains the software instructions and data to facilitate operation as described herein. The control circuitry 166 may be associated with a communication interface 170, which is to be coupled to the driver module 130, either directly or indirectly via the communication bus. The control circuitry 166 may be associated with a wired communication port 172, a wireless communication port 174, or both, to facilitate wired or wireless communications with other lighting devices 110A-110N, one or more user input devices 136, and remote control entities. The wireless communication port 174 may include the requisite transceiver electronics to facilitate wireless communications with remote entities. The wired communication port 172 may support universal serial (USB), Ethernet, or like interfaces.

Capabilities of the communication module 132 may vary from one embodiment to another. For example, the communication module 132 may act as a simple bridge between the driver module 130 and the other lighting devices 110A-110N or remote control entities. In such an embodiment, the control circuitry 166 may primarily pass data and instructions received from the other lighting fixtures 110 or remote control entities to the driver module 130, and vice-versa. The control circuitry 166 may translate the instructions as necessary based on the protocols being used to facilitate communications between the driver module 130 and the communications module 132 as well as between the communication module 132 and any remote control entities.

In other embodiments, the control circuitry 166 may play an important role in coordinating intelligence and sharing data among the lighting devices 110A-110N as well as providing significant, if not complete, control of the driver module 130. The control circuitry 166 may also be configured to receive data and instructions from the other lighting devices 110A-110N or remote control entities and use this information to control the driver module 130. The communication module 132 may also provide instructions to other lighting devices 110A-110N and remote control entities based on data received from the driver module 130 and/or the sensor module 140, as well as data and instructions received from any remote entitles and/or other lighting devices 110A-110N.

Power for the control circuitry 166, memory 168, the communication interface 170, and the wired and/or wireless communication ports 172 and 174 may be provided over the power bus via the power port. As noted above, the power bus may receive its power from the driver module 130, which generates a DC power signal. As such, the communication module 132 may not need to be connected to AC power or include rectifier and conversion circuitry. The power port and the communication port may be separate or may be integrated with the standard communication interface. The power port and communication port are shown separately for clarity. In one embodiment, the communication bus is a 2-wire serial bus, wherein the connector or cabling configuration may be configured such that the communication bus and the power bus are provided using four wires: data, clock, power, and ground. In alternative embodiments, an internal power supply 176 may be associated with AC power or a battery, and may be used to supply power to the communication module 132.

With continued reference to FIG. 8, the communication module 132 may include a status indicator, such as an LED 178 to indicate the operating state of the communication module 132. Further, a user interface 180 may be provided to allow a user to manually interact with the communication module 132. The user interface 180 may include an input mechanism, an output mechanism, or both. An input mechanism may include one or more of buttons, keys, keypads, touchscreens, or the like. An output mechanism may include one more LEDs, a display, or the like. The term "button" as used herein may include a push button switch, all or part of a toggle switch, rotary dial, slider, or any other mechanical input mechanism.

Figure 9:
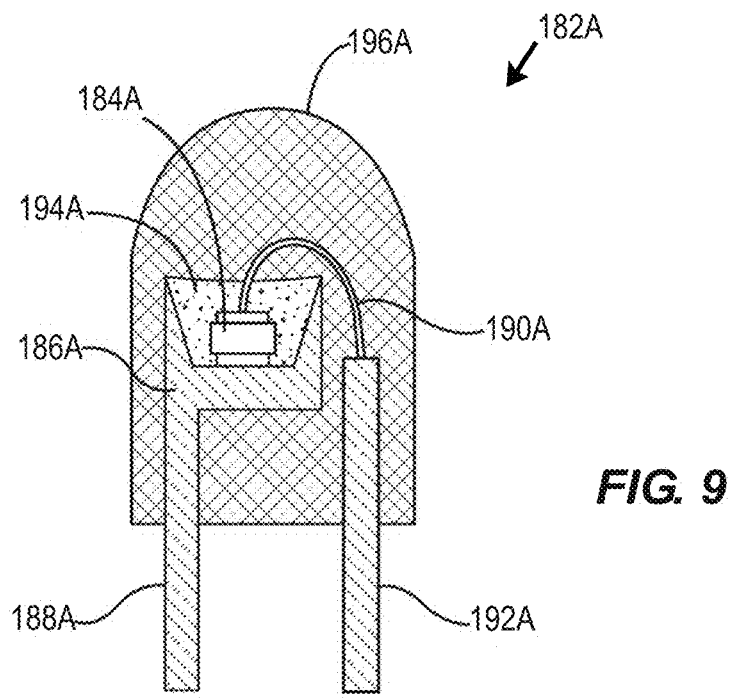
FIG. 9 is a simplified cross-sectional view of a first exemplary LED useable with lighting devices and systems according to the disclosure.

A description of an exemplary embodiment of the LED array 120, driver module 130, and the communication module 132 follows. The LED array 120 includes a plurality of LEDs, which may be embodied in LEDs 182A and/or LEDs 182B illustrated in FIGS. 9 and 10. With reference to FIG. 9, a single LED chip 184A is mounted on a reflective cup 186A using solder or a conductive epoxy, such that ohmic contacts for the cathode (or anode) of the LED chip 184A are electrically coupled to the bottom of the reflective cup 186A. The reflective cup 186A is either coupled to or integrally formed with a first lead 188A of the LED 182A. One or more bond wires 190A connect ohmic contacts for the anode (or cathode) of the LED chip 184A to a second lead 192A.

The reflective cup 186A may be filled with an encapsulant material 194A that encapsulates the LED chip 184A. The encapsulant material 194A may be clear or contain a wavelength conversion material, such as a phosphor or other lumiphoric material. The entire assembly is encapsulated in a clear protective resin 196A, which may be molded in the shape of a lens to control the light emitted from the LED chip 184A.

Figure 10:
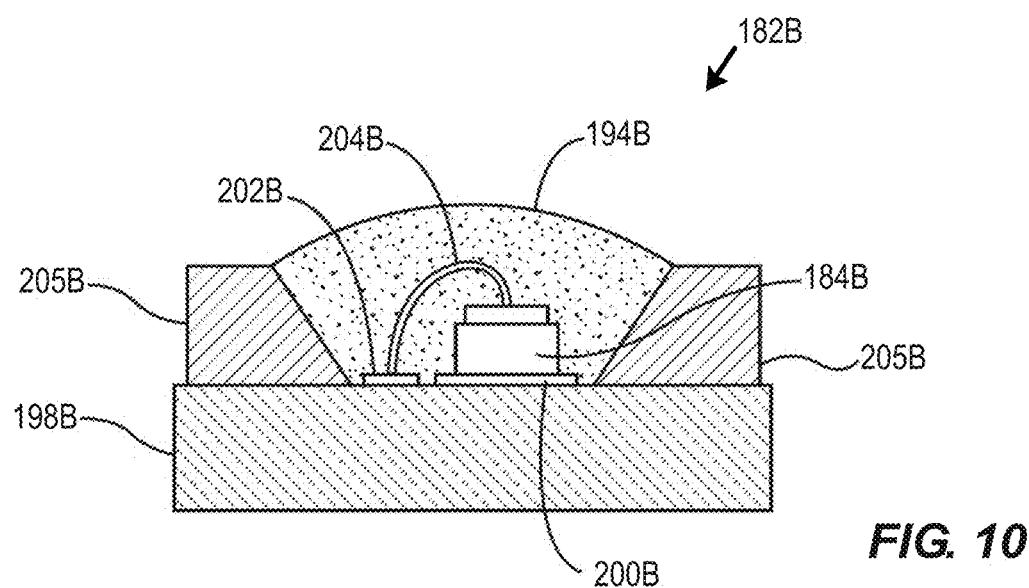
FIG. 10 is a simplified cross-sectional view of a second exemplary LED useable with lighting devices and systems according to the disclosure.

An alternative LED package 182B is illustrated in FIG. 10 wherein the LED chip 184B is mounted on a substrate 198B. In particular, the ohmic contacts for the anode (or cathode) of the LED chip 184B are directly mounted to first contact pads 200B on the surface of the substrate 198B. The ohmic contacts for the cathode (or anode) of the LED chip 184B are connected to second contact pads 202B, which are also on the surface of the substrate 198B, using bond wires 204B. The LED chip 184B resides in a cavity of a reflector structure 205B, which is formed from a reflective material and functions to reflect light emitted from the LED chip 184B through the opening formed by the reflector structure 205B. The cavity formed by the reflector structure 205B may be filled with an encapsulant material 194B that encapsulates the LED chip 184B. The encapsulant material 194B may be clear or contain a wavelength conversion material, such as a phosphor or other lumiphoric material.

In either of the embodiments of FIGS. 9 and 10, if the encapsulant material 194A, 194B is clear, then the light emitted by the respective LED chip 184A, 184B passes through the encapsulant material 194A, 194B and the protective resin 196A without any substantial shift in color. Alternatively, if the encapsulant material 194A, 194B contains a wavelength conversion material, then some or all emissions of the LED chip 184A, 184B in a first wavelength range may be absorbed by the wavelength conversion material, which will responsively emit light in a second wavelength range. The concentration and type of wavelength conversion material will dictate how much of the light emitted by the LED chip 184A, 184B is absorbed by the wavelength conversion material as well as the extent of the wavelength conversion. In embodiments where some of the light emitted by the LED chip 184A, 184B passes through the wavelength conversion material without being absorbed, light passing through the wavelength conversion material will mix with light emitted by the wavelength conversion material. Thus, when a wavelength conversion material is used, the light emitted from the LED package 182A, 182B is shifted in color from the actual light emitted from the LED chip 184A, 184B contained therein.

A generic LED package that may embody features of either the LED package 182A or the LED package 182B is referred to herein as "LED 182" and a generic LED chip such as may be embodied in LED chip 184A or LED chip 184B is referred to herein as "LED chip 184."

For example, a LED array 120 may include a group of blue shifted yellow ("BSY") or blue shifted green ("BSG") LEDs 182 as well as a group of red LEDs 182. A BSY LED 182 includes a LED chip 184 that emits bluish light, and a wavelength conversion material such as a yellow phosphor that absorbs at least a portion of the blue light and emits yellowish light. The resultant mixture of light emitted from the overall BSY LED 182 may embody yellowish light having a color point falling above the Planckian or Black Body Locus (BBL) on a 1976 CIE chromaticity diagram, wherein the BBL corresponds to the various color temperatures of white light.

In a similar manner, BSG LEDs 182 include a LED chip 184 that emits bluish light in combination with a wavelength conversion material such as a greenish phosphor that absorbs at least a portion of the blue light and emits greenish light. The resultant mixture of light emitted from the overall BSG LED 182 may embody greenish light having a color point falling above the BBL on a 1976 CIE chromaticity diagram.

Red LEDs 182 generally emit reddish light at a color point on the opposite side of the BBL as the yellowish or greenish light of BSY or BSG LEDs 182A, 182B. As such, the reddish light from red LEDs 182 may mix with yellowish or greenish light emitted from BSY or BSG LEDs 182 to generate white light that has a desired color temperature and falls within a desired proximity of the BBL. In effect, the reddish light from the red LEDs 182 "pulls" aggregated emissions including the yellowish or greenish light from the BSY or BSG LEDs 182 to a desired color point on or near the BBL. Red LEDs 182 may include LED chips 184 that natively emit reddish light in the absence of wavelength conversion material, or alternatively may include a red-emitting wavelength conversion material arranged to be stimulated by a shorter wavelength (e.g., UV- or blue-emitting) LED wherein the wavelength conversion material generates reddish light.

A blue LED chip 184 used to form either a BSY or BSG LED 182 may be formed from a gallium nitride (GaN), indium gallium nitride (InGaN), silicon carbide (SiC), zinc selenide (ZnSe), or a like material system. A red LED chip 184 may be formed from an aluminum indium gallium nitride (AlInGaP), gallium phosphide (GaP), aluminum gallium arsenide (AlGaAs), or a like material system. Exemplary yellow phosphors include cerium-doped yttrium aluminum garnet (YAG:Ce), yellow BOSE (Ba, O, Sr, Si, Eu) phosphors, and the like. Exemplary green phosphors include green BOSE phosphors, Lutetium aluminum garnet (LuAg), cerium doped LuAg (LuAg:Ce), and the like. The above-described and illustrated LED architectures, phosphors, and material systems are merely exemplary and are not intended to provide an exhaustive listing of architectures, phosphors, and materials systems that are applicable to the concepts disclosed herein.

Figure 11:
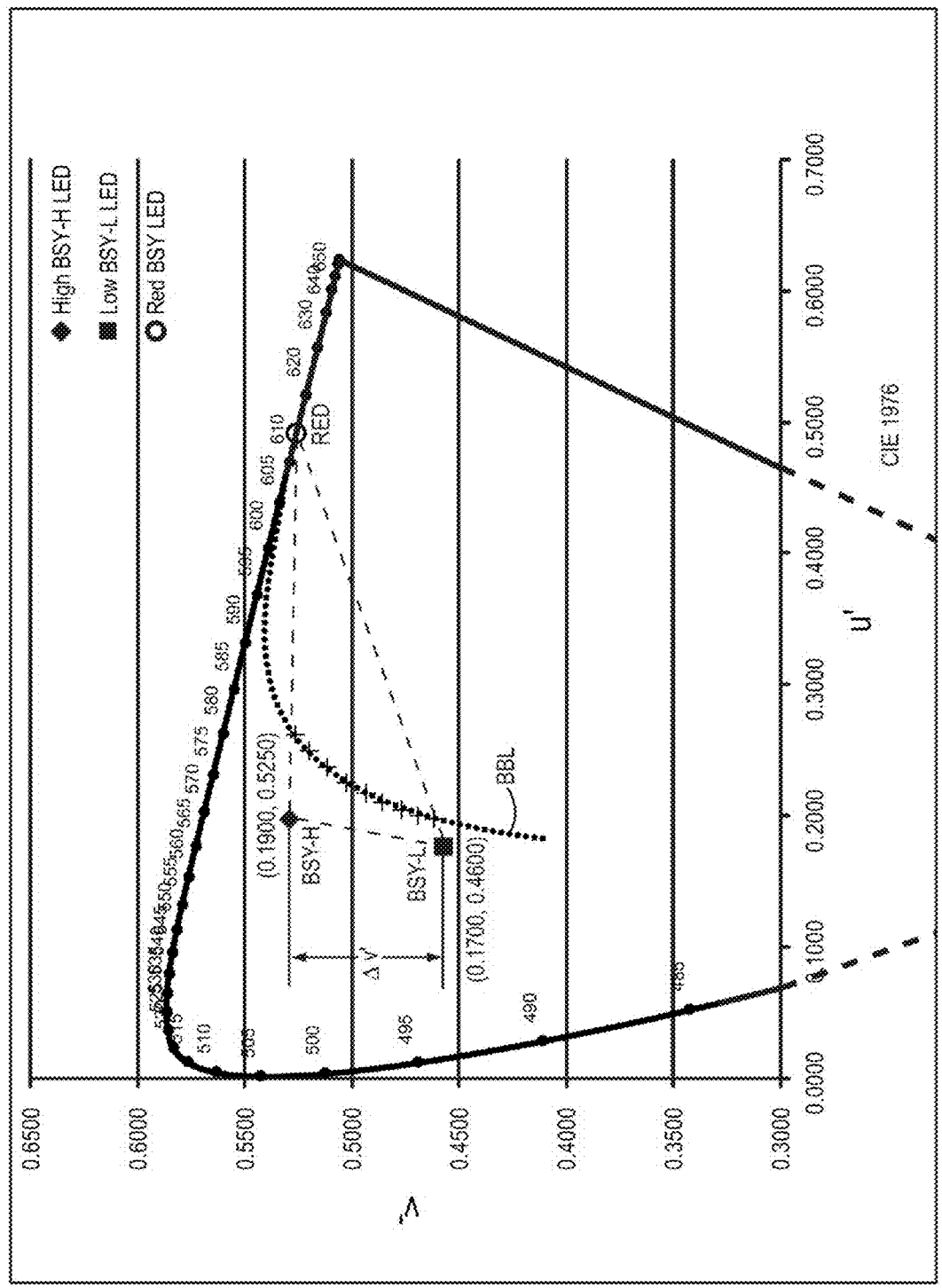
FIG. 11 illustrates a portion of a CIE 1976 chromaticity diagram including the blackbody locus, with addition of a triangle defined by color points of a first blue-shifted yellow LED, a second blue-shifted yellow LED, and a red LED.

FIG. 11 illustrates a portion of a CIE 1976 chromaticity diagram including the blackbody locus, with addition of a triangle defined by color points of a first blue-shifted yellow LED, a second blue-shifted yellow LED, and a red LED. The coordinates (u', v') are used to define color points within the color space of the CIE 1976 chromaticity diagram. The v' value defines a vertical position and the u' value defines a horizontal position. As an example, the color points for a first BSY LED 182 is about (0.1900, 0.5250), a second BSY LED 182 is about (0.1700, 0.4600), and a red LED 82 is about (0.4900, 0.5250). Notably, the first and second BSY LEDs 182 are significantly spaced apart from one another along the v' axis, with the color point of the first BSY LED 82 being much higher than the second BSY LED 182 in the chromaticity diagram. For ease of reference, the higher, first BSY LED 182 is referenced as the high BSY-H LED, and the lower, second BSY LED 82 is referenced as the low BSY-L LED 182.

The $\Delta v'$ value for the high BSY-H LED and the low BSY-L LED is about 0.065 in the illustrated example. In different embodiments, the $\Delta v'$ value may be greater than 0.025, 0.030, 0.033, 0.040, 0.050, 0.060, 0.075, 0.100, 0.110, and 0.120, respectively. Exemplary upper bounds for $\Delta v'$ may be 0.150, 0.175, or 0.200 for any of the aforementioned lower bounds. For groups of LEDs of a particular color, the $\Delta v'$ between two groups of LEDs is the difference between the average v' values for each group of LEDs. The $\Delta v'$ value between groups of LEDs of a particular color may also be greater than 0.030, 0.033, 0.040, 0.050, 0.060, 0.075, 0.100, 0.110, and 0.120, respectively, with the same upper bounds as described above. Further, the variation of color points among the LEDs 182 within a particular group of LEDs may be limited to within a seven, five, four, three, or two-step MacAdam ellipse in certain embodiments. In general, the greater the $\Delta v'$ value, the larger the range through which the CCT of the white light can be adjusted along the BBL. The closer the white light is to the BBL, the more closely the white light will replicate that of an incandescent radiator.

In one embodiment, a LED array 20 may include a first LED group of only low BSY-L LEDs, a second LED group of only high BSY-H LEDs, and a third LED group of only red LEDs. The currents used to drive the first, second, and third LED groups may be independently controlled such that the intensity of the light output from the first, second, and third LED groups is independently controlled. As such, light output of the first, second, and third LED groups may be blended or mixed to generate light having an overall color point virtually anywhere within a triangle formed by the color points of the respective low BSY-L LEDs, high BSY-H LEDs, and the red LEDs. Within this triangle resides a significant portion of the BBL, such that the overall color point of the light output may be dynamically adjusted to fall along the portion of the BBL that resides within the triangle.

A crosshatch pattern highlights the portion of the BBL that falls within the triangle. Adjusting the overall color point of the light output along the BBL corresponds to adjusting the CCT of the light output, which as noted above is considered white light when falling on the BBL. In one embodiment, the CCT of the overall light output may be adjusted over a range from about 2700 K to about 5700 K. In another embodiment, the CCT of the overall light output may be adjusted over a range from about 3000 K to 5000 K. In yet another embodiment, the CCT of the overall light output may be adjusted over a range from about 2700 K to 5000 K. These variations in CCT can be accomplished while maintaining a high color rendering index value (CRI), such as a CRI equal to or greater than 90.

To be considered "white" light, the overall color point does not have to fall precisely on the BBL. Unless defined otherwise and for the purposes of this application only, a color point within a five-step MacAdam ellipse of the BBL is defined as white light on the BBL. For tighter tolerances, four, three, and two-step MacAdam ellipses may be defined.

As noted previously, a LED array 120 may include a mixture of red LEDs 182, high BSY-H LEDs 182, and low BSY-L LEDs 182. Although the preceding discussion has emphasized mixtures of light falling on or near the BBL, it is to be emphasized that multiple LEDs may be driven to provide aggregate output having color points non-coincident with the BBL if desired.

Figure 12:
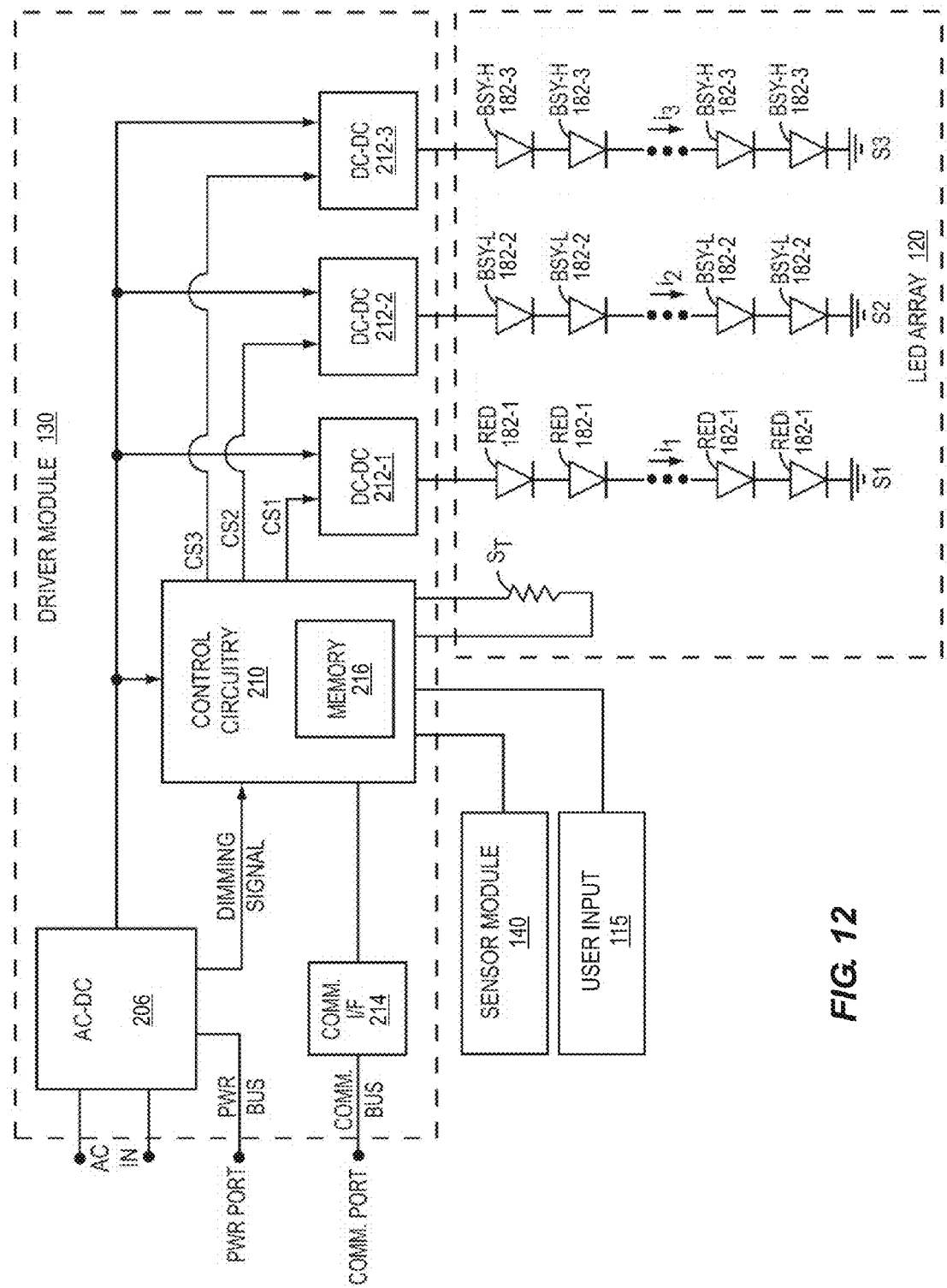
FIG. 12 is a schematic view of a driver module and a LED array including multiple separately controllable strings of LEDs according to one embodiment of the disclosure.

FIG. 12 illustrates a driver module 130 for driving a LED array 120 according to one embodiment of the disclosure. The LED array 120 may be divided into multiple strings of series-connected LEDs 182. A first LED string S1 includes multiple red LEDs 182-1, a second LED string S2 includes multiple low BSY LEDs 182-2, and a third LED string S3 includes multiple high BSY LEDs 182-3.

For clarity, the various LEDs of the LED array 120 are referenced as RED, BSY-L, and BSY-H in FIG. 12 to clearly indicate which LEDs are located in the various LED strings S1, S2, and S3. While BSY LEDs 182-2, 182-3 are illustrated, BSG or other wavelength converted (e.g., phosphor coated) LEDs may be employed in analogous fashion. For example, a string of high BSG-H LEDs 182-3 may be combined with a string of low BSG-L LEDs 182-2, and vice versa. Further, a string of low BSY-L LEDs 182-2 and/or high BSG-H LEDs 182-3 may be combined with one or more red LED, and vice versa. Non-phosphor-converted LEDs of various colors, such as non-wavelength converted red, amber, green, cyan, and blue LEDs, may also be employed in certain embodiments.

In general, the driver module 130 controls the currents $i_1$, $i_2$, and $i_3$ that are used to drive the respective LED strings S1, S2, and S3. The ratio of currents $i_1$, $i_2$, and $i_3$ provided to the respective LED strings S1, S2, and S3 may be adjusted to effectively control the relative intensities of the reddish light emitted from the red LEDs 182-1 of LED string S1, the yellowish/greenish light emitted from the low BSY-L LEDs 182-2 of LED string S2, and the yellow/greenish light emitted from the high BSY-H LEDs 182-3 of LED string S3. The resultant light from each LED string S1, S2, and S3 mixes to generate an overall light output that has a desired color, CCT, and intensity (which may also be referred to as a dimming level). The overall light output may be white light that falls on or within a desired proximity of the BBL and has a desired CCT.

The number of LED strings S1, S2, S3 may vary from one to many and different combinations of LED colors may be used in the different strings. Each LED string S1, S2, S3 may have LEDs 182 of the same color, variations of the same color, or substantially different colors. In the illustrated embodiment, each LED string S1, S2, S3 is configured such that all of the LEDs 182-1, 182-2, 182-3 within each individual string are all essentially identical in color. However, in certain embodiments, the LEDs 182-1, 182-2, 182-3 in each string may vary substantially in color or embody completely different colors in certain embodiments. In certain embodiments, three LED strings S1, S2, S3 with red, green, and blue LEDs may be used, wherein each LED string S1, S2, S3 embodies LED dedicated to a single color. In yet another embodiment, at least two LED strings S1, S2 may be used, wherein different colored BSY or BSG LEDs are used in one LED string S1 and red LEDs are used another LED string S2. A single string embodiment is also envisioned, where currents may be individually adjusted for the LEDs of the different colors using controllable bypass circuits, controllable shunt circuits, or the like.

The driver module 130 illustrated in FIG. 12 generally includes AC-DC conversion circuitry 206, control circuitry 210, and a number of current sources, such as the illustrated DC-DC converters 212. In certain embodiments, signals from one or more user input elements 130 may be communicated directly to the driver module 115, or alternatively through the communication module 132. The AC-DC conversion circuitry 206 is adapted to receive an AC power signal (AC IN), rectify the AC power signal, correct the power factor of the AC power signal, and provide a DC output signal. The DC output signal may be used to directly power the control circuitry 210 and any other circuitry provided in the driver module 130, including the DC-DC converters 212, a communication interface 214, and the sensor module 140.

The DC output signal may also be provided to the power bus, which is coupled to one or more power ports (e.g., as part of a standard communication interface). The DC output signal provided to the power bus may be used to provide power to one or more external devices that are coupled to the power bus and separate from the driver module 130. These external devices may include the communication module 132 and any number of auxiliary devices, such as the sensor module 140.

As illustrated, the three respective DC-DC converters 212-1, 212-2, 212-3 of the driver module 130 provide currents $i_1$, $i_2$, and $i_3$ for the three LED strings S1, S2, and S3 in response to control signals CS1, CS2, and CS3. The control signals CS1, CS2, and CS3 may be pulse width modulated (PWM) signals that effectively turn the respective DC-DC converters 212-1, 212-2, 212-3 on during a logic high state and off during a logic low state of each period of the PWM signal.

In certain embodiments the control signals CS1, CS2, and CS3 may be the product of two PWM signals. The first PWM signal is a higher frequency PWM signal that has a duty cycle that effectively sets the DC current level through a corresponding one of LED strings S1, S2, and S3, when current is allowed to pass through the LED strings S1, S2, and S3. The second PWM signal is a lower frequency signal that has a duty cycle that corresponds a desired dimming or overall output level. In essence, the higher frequency PWM signals set the relative current levels though each LED string S1, S2, and S3 while the lower frequency PWM signal determines how long the currents $i_1$, $i_2$, and $i_3$ are allowed to pass through the LED strings S1, S2, and S3 during each period of the lower frequency PWM signal. The longer the currents $i_1$, $i_2$, and $i_3$ are allowed to flow through the LED strings S1, S2, and S3 during each period, the higher the output level, and vice versa. Given the reactive components associated with the DC-DC converters 212, the relative current levels set with the higher frequency PWM signals may be filtered to a relative DC current. However, this DC current is essentially pulsed on and off based on the duty cycle of the lower frequency PWM signal. In one embodiment, the higher frequency PWM signal may have a switching frequency of around 200 KHz, while the lower frequency PWM signal may have a switching frequency of around 1 KHz.

In certain embodiments, a dimming device may control the AC power signal. The AC-DC conversion circuitry 206 may be configured to detect the relative amount of dimming associated with the AC power signal and provide a corresponding dimming signal to the control circuitry 210. Based on the dimming signal, the control circuitry 210 will adjust the currents $i_1$, $i_2$, and $i_3$ provided to each of the LED strings S1, S2, and S3 to effectively reduce the intensity of the resultant light emitted from the LED strings S1, S2, and S3 while maintaining the desired CCT. As described further below, the CCT and dimming levels may be initiated internally or received from the user input element 136, a wall controller, or another lighting device. If received from an external device via the communication module 132, the color point, CCT level, and/or dimming levels are delivered from the communication module 132 to the control circuitry 210 of the driver module 130 in the form of a command via the communication bus. The driver module 130 will respond by controlling the currents $i_1$, $i_2$, and $i_3$ in the desired manner to achieve the requested CCT and/or dimming levels.

The intensity and CCT of light emitted by the LEDs 182 may be affected by temperature. If associated with a thermistor $S_T$ or other temperature-sensing device, the control circuitry 210 can control the currents $i_1$, $i_2$, and $i_3$ provided to each of the LED strings S1, S2, and S3 based on ambient temperature of the LED array 120 in an effort to compensate for temperature effects. The control circuitry 210 may also monitor the output of the occupancy and ambient light sensors $S_O$ and $S_A$ for occupancy and ambient light information and further control the currents $i_1$, $i_2$, and $i_3$ in a desired fashion. Each of the LED strings S1, S2, and S3 may have different temperature compensation adjustments, which may also be functions of the magnitude of the various currents $i_1$, $i_2$, and $i_3$.

The control circuitry 210 may include a central processing unit (CPU) and sufficient memory 216 to enable the control circuitry 210 to bidirectionally communicate with the communication module 132 or other devices over the communication bus through an appropriate communication interface (I/F) 214 using a defined protocol, such as the standard protocol described above. The control circuitry 210 may receive instructions from the communication module 132 or other device and take appropriate action to implement the received instructions. The instructions may include controlling how the LEDs 182 of the LED array 120 are driven, or returning operational data, such as temperature, occupancy, light output, or ambient light information, that was collected by the control circuitry 210 to the communication module 132 or other device via the communication bus. In certain embodiments, the functionality of the communication module 132 may be integrated into the driver module 130, and vice versa.

In certain embodiments, the control circuitry 210 of the driver module 130 is loaded with a current model in the form of one or more functions (equation) or look up tables for each of the currents $i_1$, $i_2$, and $i_3$. Each current model is a reference model that is a function of dimming or output level, temperature, and CCT. The output of each model provides a corresponding control signal CS1, CS2, and CS3, which effectively sets the currents $i_1$, $i_2$, and $i_3$ in the LED strings S1, S2, and S3. The three current models are related to each other. At any given output level, temperature, and CCT, the resulting currents $i_1$, $i_2$, and $i_3$ cause the LED strings S1, S2, and S3 to emit light, which when combined, provides an overall light output that has a desired output level and CCT, regardless of temperature. While the three current models do not need to be a function of each other, they are created to coordinate with one another to ensure that the light from each of the strings S1, S2, and S3 mix with one another in a desired fashion.

The above-mentioned current model stored in memory 216 of the control circuitry 210 may correspond to a base schedule or emitter operating schedule as described herein. Such base schedule may operate the lighting device 110 based on the geospatial location and the date/time. The base schedule in such embodiment may be reestablished on a periodic (e.g., daily, weekly, monthly, or seasonally) basis and automatically altered from day to day, from week to week, from month to month, or from season to season such that one or more electrically activated emitters are operated differently on different days of a year. Additionally, brightness and/or spectral content of the emissions of the lighting device may be further adjusted intraday based on sensed ambient conditions, sensed conditions of an illuminated space or surface, information indicative of weather conditions, and/or user inputs.

Although the preceding discussion of LEDs 182 has been directed primarily to single-chip LED packages, in certain embodiments lighting devices described herein may include multi-chip LED packages with separately controllable LED chips. FIG. 13A illustrates a solid state emitter package 300 including multiple solid state light emitters (e.g., LED chips). The emitter package 300 includes multiple (e.g., four) LED chips 350A-350D that may be separately controlled (e.g., via backside anodes 321A-321D and cathodes 322A-322D) and that are supported by an insulating substrate 310. The substrate 310, which may preferably comprise a ceramic material, includes an upper surface 311, a lower surface 312, and side walls 313-316 extending between the upper surface 311 and the lower surface 312. Electrical traces 340 are arranged over the substrate 310, including multiple die attach pads 341A-341D and additional electrical elements 342A-342D arranged proximate to the die attach pads 341A-341D. Where the die attach pads 341A-341D are electrically conductive, the LED chips 350A-350D may be arranged with bottom side contacts thereof in electrical communication with the die attach pads 341A-314D, and with top side contacts thereof in electrical communication with the electrical elements 342A-342D by way of wirebonds 352. The die attach pads 341A-341D and electrical elements 342A-342D may comprise one or more metals patterned on (or in) the upper surface 311 of the substrate 310. Gaps 345 may be provided between adjacent die attach pads 341A-341D and/or electrical elements 342A-342D to prevent undesired conductive electrical communication. In certain embodiments, die attach pads need not be electrically conductive, such as in cases where anode and cathode connections to a solid state emitter chip are both made with wirebonds. An insulating soldermask 347 is patterned over peripheral portions of the electrical traces 340, and a molded lens 360 (e.g., including a raised or hemispherical portion 361 and a base portion 362) is arranged over the upper surface 311 of the substrate 310 and is arranged to transmit at least a portion of light generated by the emitter chips 350A-350D.

LED chips 350A-350D of any suitable peak wavelength (e.g., color) may be used, and one, some, or all of the chips 350A-350D may be arranged to stimulate emissions of one or more lumiphors (e.g., phosphors). Although some or all of the LED chips 350A-350D may be separately controlled, in certain embodiments groups of two or more LED chips 350A-350D or groups of LED chips may be controlled together in a groupwise fashion. As noted previously, the package 300 may embody one or more LED components, with each LED component comprising at least one LED chip 350A-350D (optionally multiple LED chips), with one or more LED chips 350A-350D optionally arranged to stimulate emissions of one or more lumiphoric materials. In certain embodiments, the solid state emitter package 300 may include two LED components, with each LED component including two LED chips 350A-350D. In certain embodiments, the solid state emitter package 300 may include one, two, three, or four LED components. Although four LED chips 350A-350D are illustrated in FIG. 13A, it is to be appreciated that a LED package may include any desirable number of LED chips, including groups of chips arranged in series, in parallel, or in series-parallel configurations.

FIG. 13B is a bottom plan view of each of the emitter package 300 of FIG. 13A. A lower surface 312 of the substrate includes four anodes 321A-321D and four cathodes 322A-322D patterned thereon (e.g., as electrical traces), with one paired anode/cathode per quadrant. The separate anodes 321A-321D and cathodes 322A-322D enable separate control of the multiple solid state emitters (e.g., LED chips) 350A-350B if desired. The various anodes 321A-321D and cathodes 322A-322D are separated by gaps that may be filled with solder mask material sections 327-1, 327-2. A thermal element (e.g., thermal spreading element) 326 may be arranged along the bottom surface 312 between the solder mask material sections 327-1, 327-2 and generally underlapping the solid state emitters 350A-350D. The thickness of the thermal element 326 may be the same as or different from (e.g., thicker than) the anodes 321A-321D and cathodes 322A-322D. As shown, the package 300 is devoid of any anode or cathode arranged on, or extending laterally beyond, any side wall 313-316 thereof.

By separately controlling different emitters (e.g., LED chips) of appropriate characteristics, the package 300 may be operated according to multiple operating states to yield aggregated emissions with different light output parameters. Examples of light output parameters that may be adjusted include: color point of emissions, color temperature of emissions, spectral content of emissions, luminous flux of emissions, and operating time. One or more emitter packages 300 may be utilized in lighting devices or lighting system as disclosed herein. In certain embodiments, such emitter packages may embody or be included in LED arrays as previously described herein.

Arrays containing various combinations of emitters (either with or without lumiphoric materials) are contemplated for use in lighting devices and lighting systems as disclosed herein. FIGS. 14A-14F schematically illustrate at least portions of various exemplary LED arrays, each including multiple LEDs and at least one lumiphoric material.

Figure 14A:
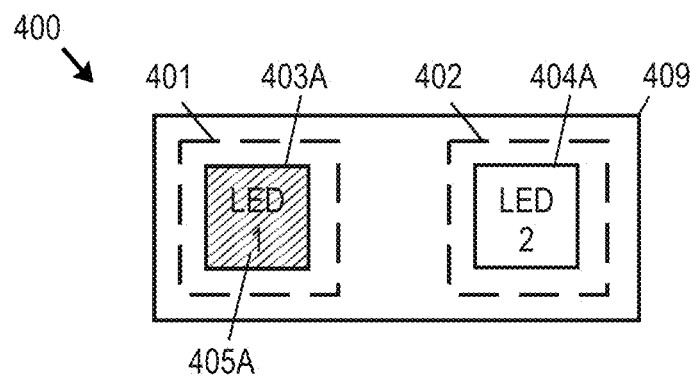
FIG. 14A is a schematic view of at least a portion of a first LED array including first and second LEDs arranged on a single submount or substrate.

FIG. 14A illustrates at least a portion of a first LED array 400 including first and second emitter components 401, 402 supported in or on a substrate or other body structure 409. The first and second emitter components 401, 402 each include at least one LED chip 403A, 404A, wherein any one or more of the LED chips 403A, 404A may be optionally arranged to stimulate emissions of one or more lumiphoric materials (e.g., such as lumiphor 405A arranged to be stimulated by LED chip 403A). Although FIG. 14A illustrates one LED chip 403A, 404A as being associated with each emitter component 401, 402, it is to be appreciated that any suitable number (e.g., two, three, four, five, six or more, etc.) of LED chips may be associated with one or more emitter components in certain embodiments.

Figure 14B:
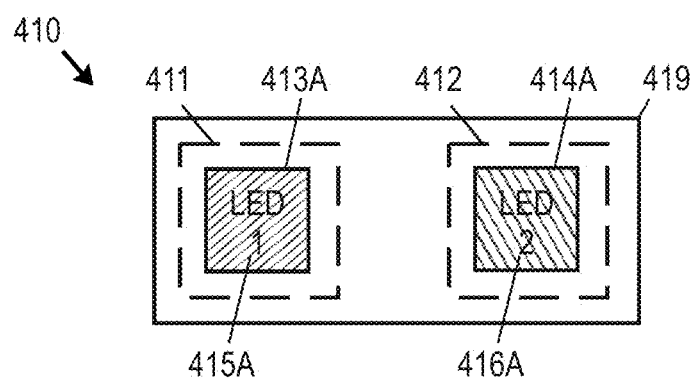
FIG. 14B is a schematic view of at least a portion of a second LED array including first and second LEDs arranged on a single submount or substrate.

FIG. 14B illustrates at least a portion of a second LED array 410 including first and second emitter components 411, 412 supported in or on a substrate or other body structure 419. The first and second emitter components 411, 412 each include at least one LED chip 413A, 414A, wherein any one or more of the LED chips 413A, 414A may be optionally arranged to stimulate emissions of one or more lumiphoric materials (e.g., such as a first lumiphor 415A arranged to be stimulated by a first LED chip 413A and a second lumiphor 416A arranged to be stimulated by a second LED chip 414A).

Figure 14C:
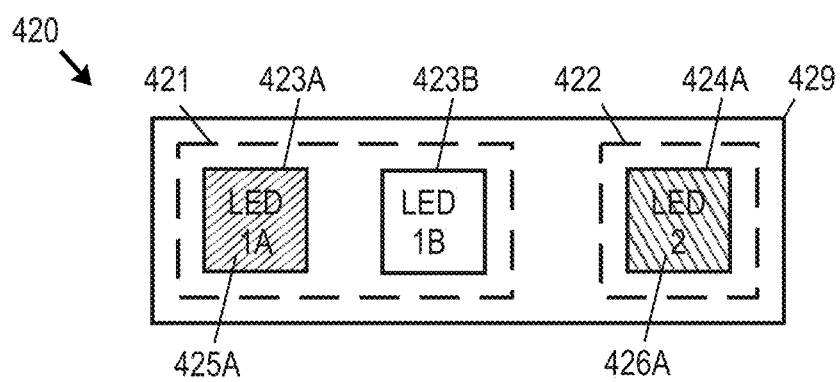
FIG. 14C is a schematic view of a at least a portion of a third LED array including a first pair of LEDs arranged in a first mounting region and another LED arranged in a second mounting region, all arranged on a single submount or substrate.

FIG. 14C illustrates at least a portion of a third LED array 420 including first and second emitter components 421, 422 supported in or on a substrate (or other body structure) 429. The first emitter component 421 includes LED chips 423A, 423B with a first LED chip 423A arranged to stimulate emissions of a first lumiphor 425A, and the second emitter component 422 includes a LED chip 424A arranged to stimulate emissions of a second lumiphor 426A. In certain embodiments, any suitable number of LED chips and lumiphors may be provided in each emitter component, and additional emitter components (not shown) may be supported by the substrate 429.

Figure 14D:
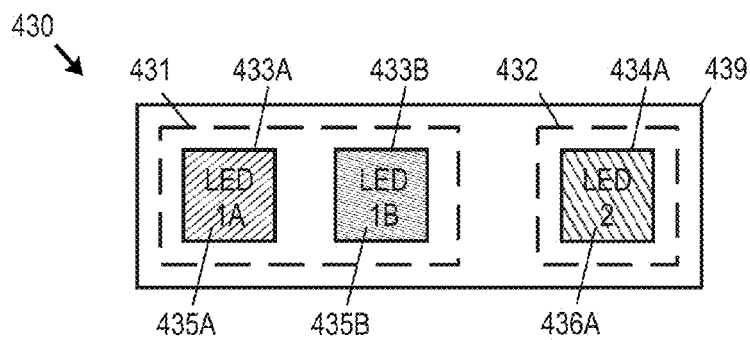
FIG. 14D is a schematic view of at least a portion of a fourth LED array including a pair of LEDs arranged in a first mounting region and another LED arranged in a second mounting region, all arranged on a single submount or substrate.

FIG. 14D illustrates at least a portion of a fourth LED array 430 including first and second emitter components 431, 432 supported in or on a substrate or other body structure 439. The first emitter component 431 includes a first LED chip 433A arranged to stimulate emissions of a first lumiphor 435A and a second LED chip 433B arranged to stimulate emissions of a second lumiphor 435B, and the second emitter component 432 includes a LED chip 434A arranged to stimulate emissions of another lumiphor 436A. In certain embodiments, any suitable number of LED chips and lumiphors may be provided in each emitter component, and additional emitter components (not shown) may be supported by the substrate 439.

Figure 14E:
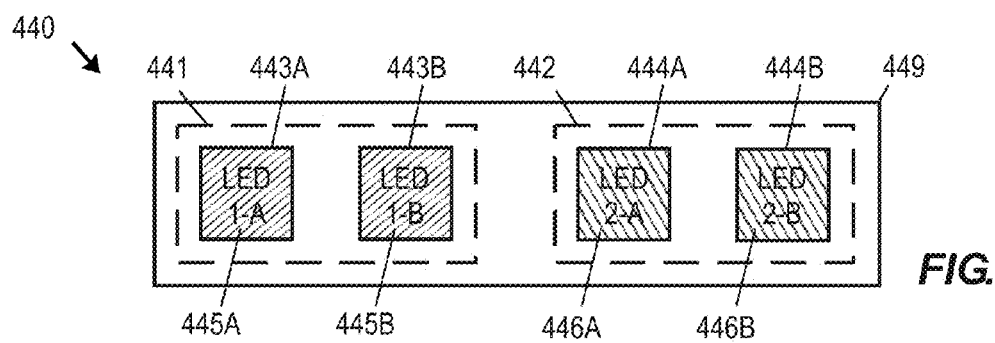
FIG. 14E is a schematic view of at least a portion of a fifth LED array including a first pair of LEDs arranged in a first mounting region and another pair of LEDs arranged in a second mounting region, all arranged on a single submount or substrate.

FIG. 14E illustrates at least a portion of a fifth LED array 440 including first and second emitter components 441, 442 supported in or on a substrate or other body structure 449. The first emitter component 441 includes a first LED chip 443A arranged to stimulate emissions of a first lumiphor 445A and a second LED chip 443B arranged to stimulate emissions of a second lumiphor 445B. The second emitter component 442 includes a first LED chip 444A arranged to stimulate emissions of a first lumiphor 446A and a second LED chip 444B arranged to stimulate emissions of a second lumiphor 446B. One or more lumiphoric materials 445A, 445B, 446A, 446B may be the same or different in the respective LED components 441, 442. In certain embodiments, any suitable number of LED chips and lumiphors may be provided in each emitter component, and additional emitter components (not shown) may be supported by the substrate 449.

Figure 14F:
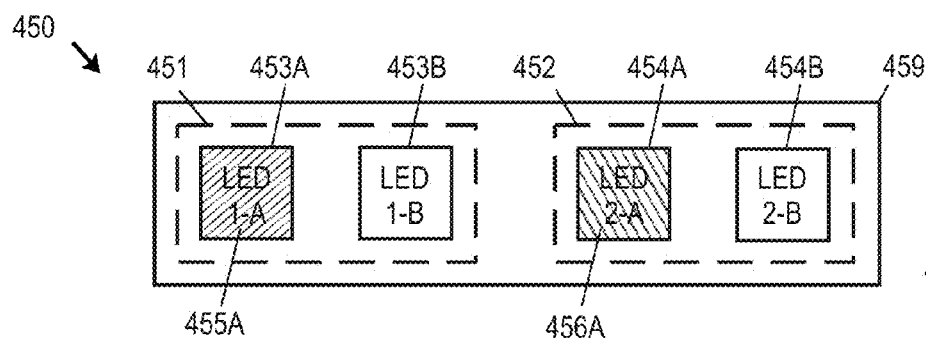
FIG. 14F is a schematic view of at least a portion of a sixth LED array including a first pair of LEDs arranged in a first mounting region and another pair of LEDs arranged in a second mounting region, all arranged on a single submount or substrate.

FIG. 14F illustrates at least a portion of a sixth LED array 450 including first and second emitter components 451, 452 supported in or on a substrate or other body structure 459. The first emitter component 451 includes a first LED chip 453A arranged to stimulate emissions of a first lumiphor 455A in addition to a second LED chip 453B, and the second emitter component 452 includes a first LED chip 454A arranged to stimulate emissions of a first lumiphor 456A in addition to a second LED chip 454B. In certain embodiments, any suitable number of LED chips and lumiphors may be provided in each emitter component, and additional emitter components (not shown) may be supported by the substrate 459.

With general reference to FIGS. 14A-14F, the first and second emitter components in each instance may embody any suitable LED chips, lumiphors, features, and/or capabilities as described herein, and are preferably separately controllable (but may be controlled together). Additional emitter components (not shown) including one or more LED chips may be further provided in or on the substrate in each instance. In embodiments including one or more emitter components with multiple LEDs, each LED within a single LED component may be individually controlled, or groups of two or more LEDs within a single component may be controlled together.

With continued reference to FIGS. 14A-14F, in certain embodiments each first emitter component may be arranged to produce emissions (or a mixture of emissions) having a first color point, each second emitter component may be arranged to produce emissions (or a mixture of emissions) having a second color point, and a mixture of light generated by the respective first and second emitter component for each device may be arranged to yield an aggregate color point. The aggregate color point may be adjusted by adjusting proportion of current to different emitter components. In certain embodiments, additional emitter components may be provided to permit further adjustment of the aggregate color point. In certain embodiments, adjustment of current or current pulse width to different emitter components may be used to adjust light output parameters such as color point of emissions, color temperature of emissions, spectral content of emissions, luminous flux of emissions, and operating time. One or more LED arrays such as described in FIGS. 14A-14F may be utilized in lighting devices or lighting system as disclosed herein.

Figure 15:
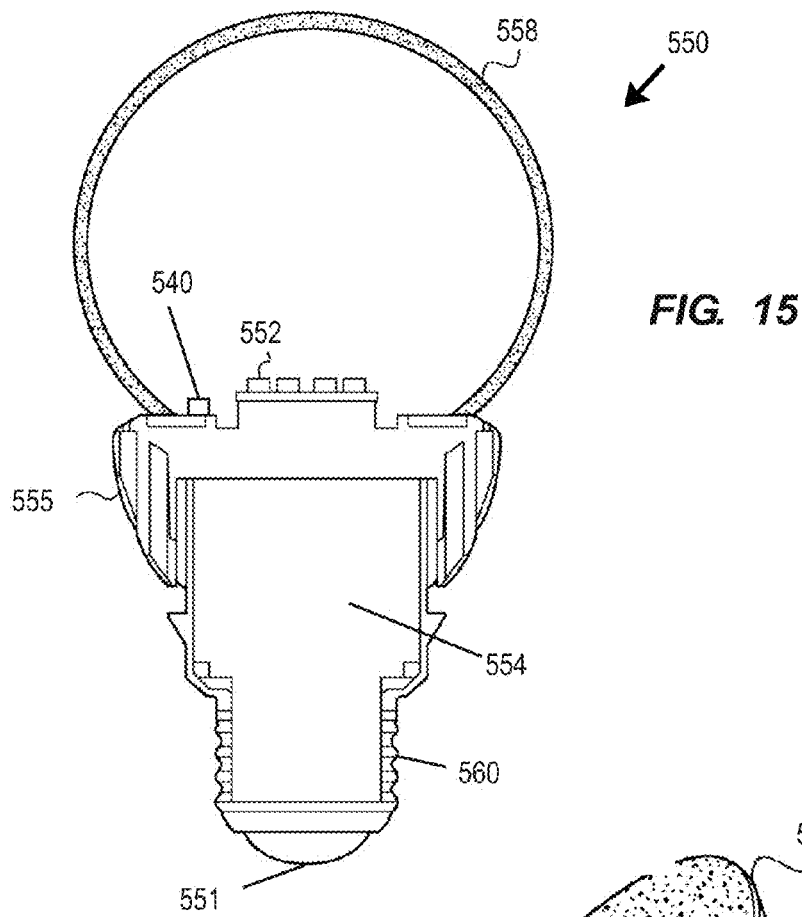
FIG. 15 is a side cross-sectional view of a first light bulb arranged to incorporate multiple solid state emitter chips as disclosed herein.

FIG. 15 illustrates a first light bulb 550 arranged to incorporate multiple solid state emitters (e.g., LEDs) as disclosed herein. The light bulb 550 includes a power supply 554, and includes a heatsink 555 including fins to promote cooling of LED chips 552 and the power supply 554. A lateral contact 560 and foot contact 551 may be compatible with an Edison-style screw-type light socket for conducting power to the light bulb 550. An optical element 558 (which may be embodied in a light-transmissive globe) is provided to protect the LED chips 552 and provide light shaping and/or diffusion utility for light emissions of the bulb 550. One or more lumiphoric materials may be associated with the LED chips 552 and/or the optical element 558 to provide wavelength conversion utility. Two or more LED chips 552 or groups thereof (optionally in conjunction with lumiphoric materials) are arranged to separately emit light with different color points, such that by separately controlling different LED chips or groups thereof, light output parameters such as color point of emissions, color temperature of emissions, spectral content of emissions, luminous flux of emissions, and operating time may be varied. One or more of sensor(s), a signal receiver, and a user input element 540 may be provided to communicate signals to a driver module (not shown). In certain embodiments, the preceding sensor(s), signal receiver, and/or user input element 540 are arranged to receive or determine information indicative of geospatial or geographic location (and optionally additional information such as time, time zone, and/or date), to permit a driver module to automatically adjust one or more light output parameters based at least in part on such information to operate the LED chips 552 differently on different days of a year.

Figure 16:
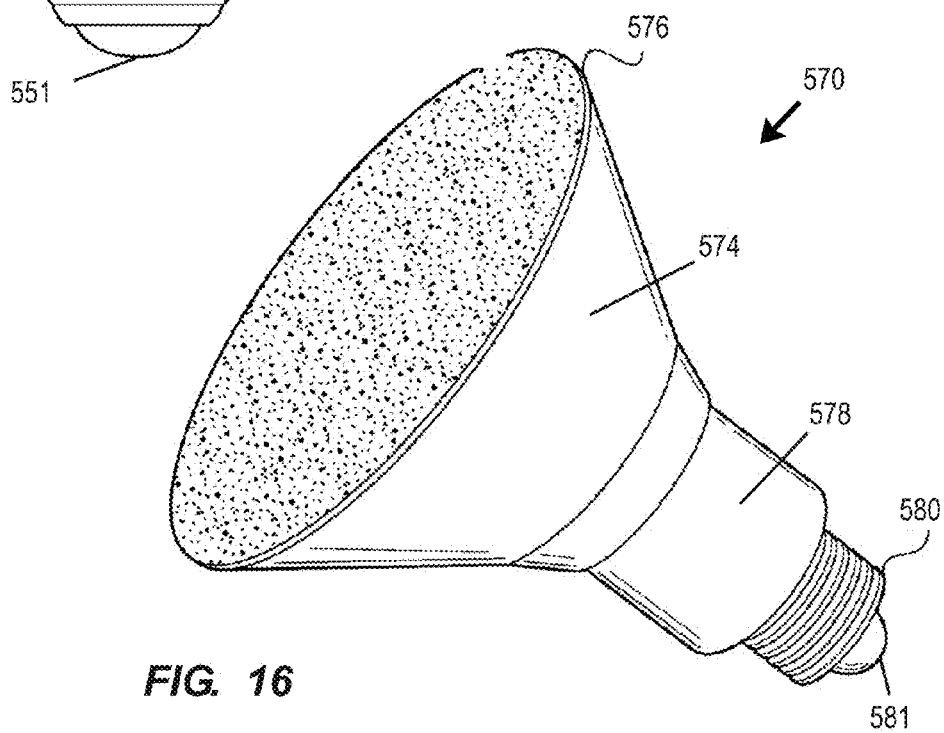
FIG. 16 is a side cross-sectional view of a second, reflector-type light bulb arranged to incorporate at least one emitter chip as disclosed herein.

FIG. 16 illustrates a second, reflector-type (i.e. PAR-style) light bulb 570 arranged to incorporate one or more groups or arrays of LEDs as disclosed herein. The light bulb 570 includes a reflector 574 and an optical element (e.g., lens) 576 covering a front or light emitting portion of the bulb 570, with the reflector 574 and lens 576 together forming a light-transmissive optical enclosure. An opposing end of the bulb includes contacts 580, 581 (e.g., an Edison-style threaded lateral contact 580 and a foot contact 581) for receiving power from a socket or other receptacle. A body structure 578 extends between the reflector 574 and a base end of the bulb 570 that includes the contacts 580, 581. The bulb 570 includes multiple LEDs (not visible) as previously discussed, and such components optionally may include one or more lumiphoric materials. Optionally, one or more light scattering and/or lumiphoric materials may be associated with the optical element 576 in certain embodiments. Two or more LED chips or groups thereof (optionally in conjunction with lumiphoric materials) may be arranged to separately emit light with different color points, such that by separately controlling different LED chips or groups thereof, light output parameters such as color point of emissions, color temperature of emissions, spectral content of emissions, luminous flux of emissions, and operating time may be varied. The light bulb 570 preferably includes at least one of a sensor, a signal receiver, and a user input element arranged to receive or determine information indicative of geospatial or geographic location (and optionally additional information such as time, time zone, and/or date), to permit automatic adjustment of one or more light output parameters based at least in part on such information to operate groups or arrays of LEDs of the light bulb 570 differently on different days of a year.

Figure 17:
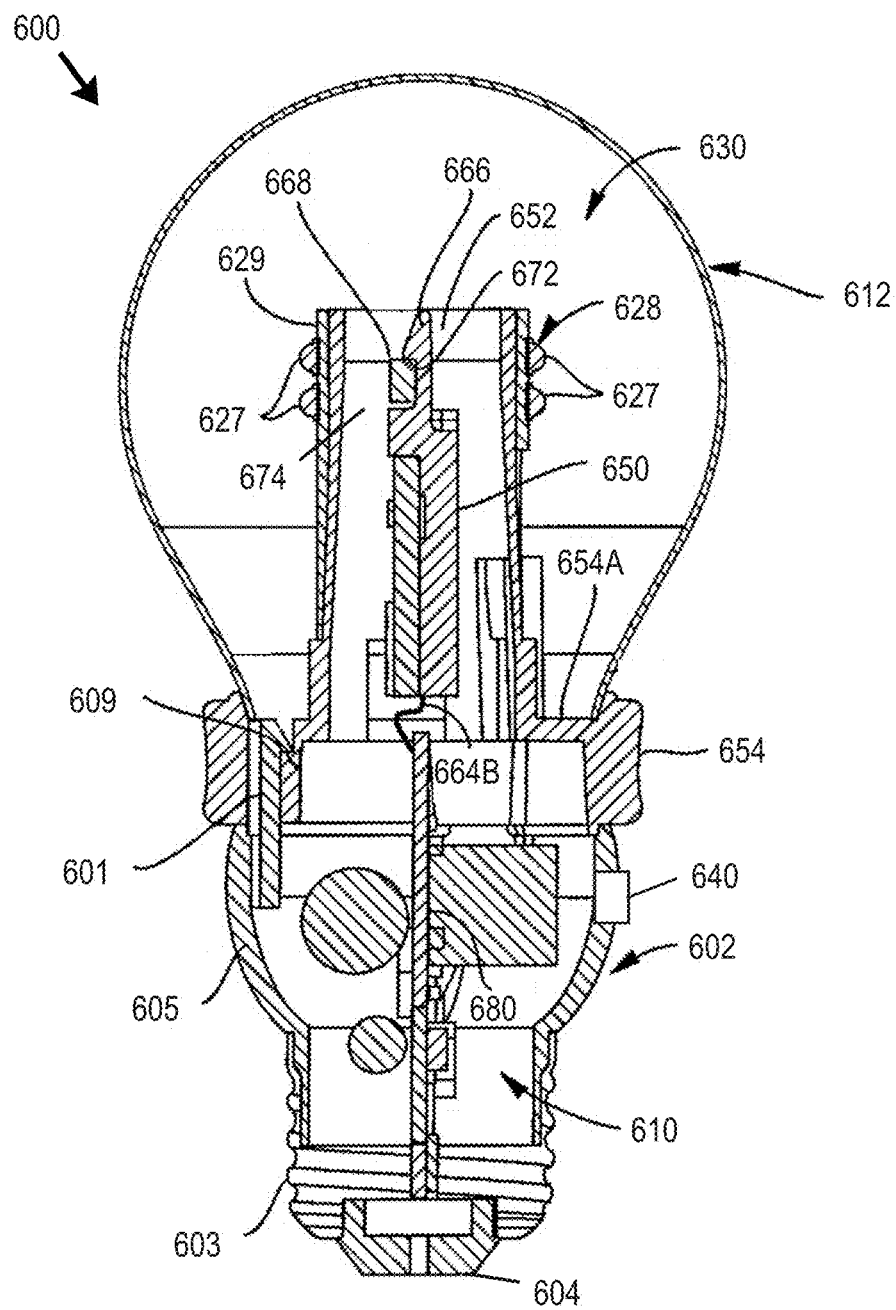
FIG. 17 is a side cross-sectional view of a third light bulb arranged to incorporate multiple solid state emitter chips as disclosed herein in a tower-type configuration.

FIG. 17 illustrates a third light bulb 600 arranged to incorporate multiple solid state emitters (e.g., LEDs) 627 as disclosed herein disposed in an array 628 in a tower-type configuration, such as disclosed in U.S. Patent Application Publication No. 2013/0271991 (incorporated by reference herein). The bulb 600 may embody an A-series bulb with an Edison base 602 including a lateral contact 603 and a foot contact 604. The base 602 may include a base printed circuit board 680 and electronics 610 within a housing 605, suitable for powering the bulb 600 and including a power supply and/or driver. The electronics 610 may be arranged in communication with at least one of a sensor, a signal receiver, and a user input element 640 arranged to receive or determine information indicative of geospatial or geographic location (and optionally additional information such as time, time zone, and/or date), to permit the electronics 610 to automatically adjust of one or more light output parameters based at least in part on such information to operate LED chips 627 of the array 628 differently on different days of a year.

The bulb 600 includes multiple LED chips 627 (of which one or more may include lumiphoric material) mounted on an upwardly-extending substantially tubular or tube-like submount (e.g., printed circuit board) 629 bounding an internal cavity 674. The LED chips 627 are operable to emit light when energized. The cavity 674 is capped by a heat conducting portion 652 that and engaging member 668 that fits with an engagement portion 666 associated with locking member 672 extending upward from an electrical interconnect 650 internal to the cavity 674. A globe-like enclosure (which may embody an optical element) 612 surrounds an interior volume containing a LED assembly 630 including the multiple emitter chips 627. A heatsink 654 is arranged between the enclosure 612 and the base 602, with a lock member 609 arranged to receive and retain deformable fingers 601 during assembly of the bulb 600. A bottom edge of the enclosure 612 abuts a top surface 654A of the heatsink 654. Internal conductors 664B are arranged to conduct electrical signals between the base PCB 680 and components of the LED assembly 630.

Figure 18A:
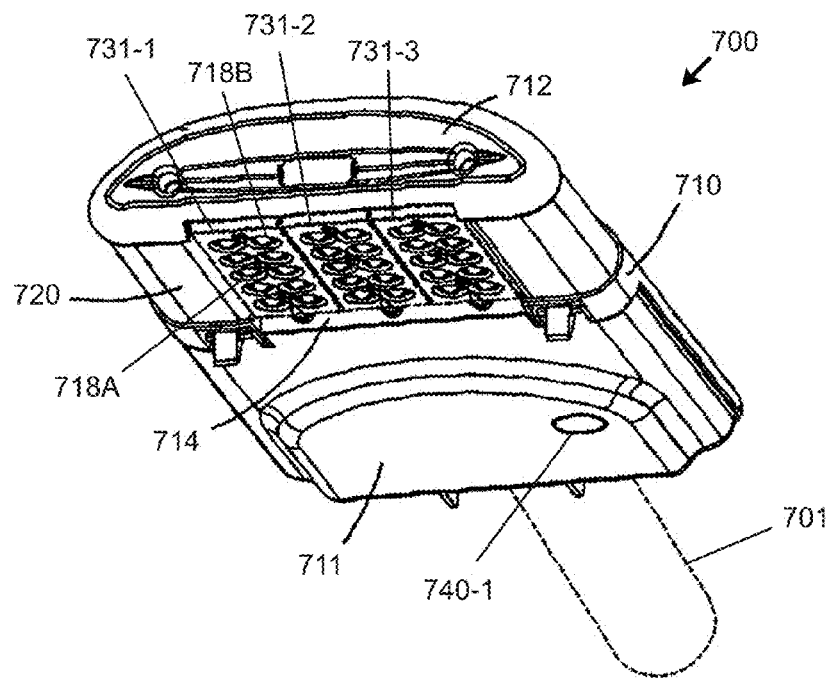
FIG. 18A is a lower perspective view of an outdoor floodlight (e.g., street or roadway lamp) including multiple solid state emitters as described herein.
Figure 18B:
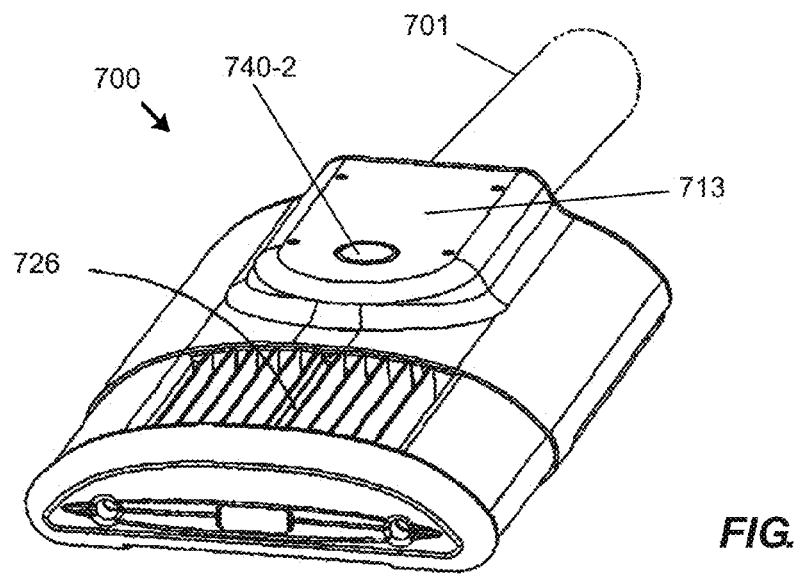
FIG. 18B is an upper perspective view of the outdoor floodlight of FIG. 18A.

In certain embodiments, at least one lumiphoric material may be associated with one or more emitter chips 627 and/or additionally associated with the enclosure (or optical element) 612. The optical element 612 may further include light scattering materials in certain embodiments. Two or more emitter chips 627 or groups thereof (optionally in conjunction with lumiphoric material and/or notch filtering material) may be arranged to generate emissions having different color points. By separately controlling different LED chips 627 or groups thereof, light output parameters such as color point of emissions, color temperature of emissions, spectral content of emissions, luminous flux of emissions, and operating time may be varied FIGS. 18A-18B illustrate an outdoor floodlight (e.g., street or roadway lamp) 700 that may include multiple LED components as described herein. The lamp 700 includes a housing 710 including a base portion 711 supported by an elongated pole 701 or other support. Multiple LEDs modules 731-1, 731-2, 731-3 each including multiple LEDs 718A, 718B arranged in an array are provided along a lower surface 720 of the floodlight 700 between the pole 701 and an end cap 712. The LED modules 731-1, 731-2, 731-3 are arranged proximate to an air gap 714 permitting heat to be dissipated to a heat spreader or heat sink 726 (arranged along an upper surface 713 of the housing 710) and transferred to an ambient environment. The floodlight 700 may include at least one receiver or sensor element 740-1, 740-2, which may embody any one or more of GPS receiver, a radio frequency receiver, an ambient light sensor, an image sensor, a temperature sensor, and occupancy sensor, a sound sensor, or the like. In certain embodiments, at least one receiver or sensor element 740-1 may be arranged along a lower surface 720 of the floodlight 700, and/or at least one receiver of sensor element 740-2 may be arranged along an upper surface of the floodlight 700. The floodlight is arranged to receive or determine information indicative of geospatial or geographic location (and optionally additional information such as time, time zone, and/or date) and automatically adjust one or more light output parameters based at least in part on such information to operate one or more electrically activated emitters differently on different days of a year. Signals received by the at least one receiver or sensor element 740-1, 740-2 may be used to control operation of the LEDs modules 731-1, 731-2, 731-3 to adjust light output parameters such as color point of emissions, color temperature of emissions, spectral content of emissions, luminous flux of emissions, and operating time.

Figure 19:
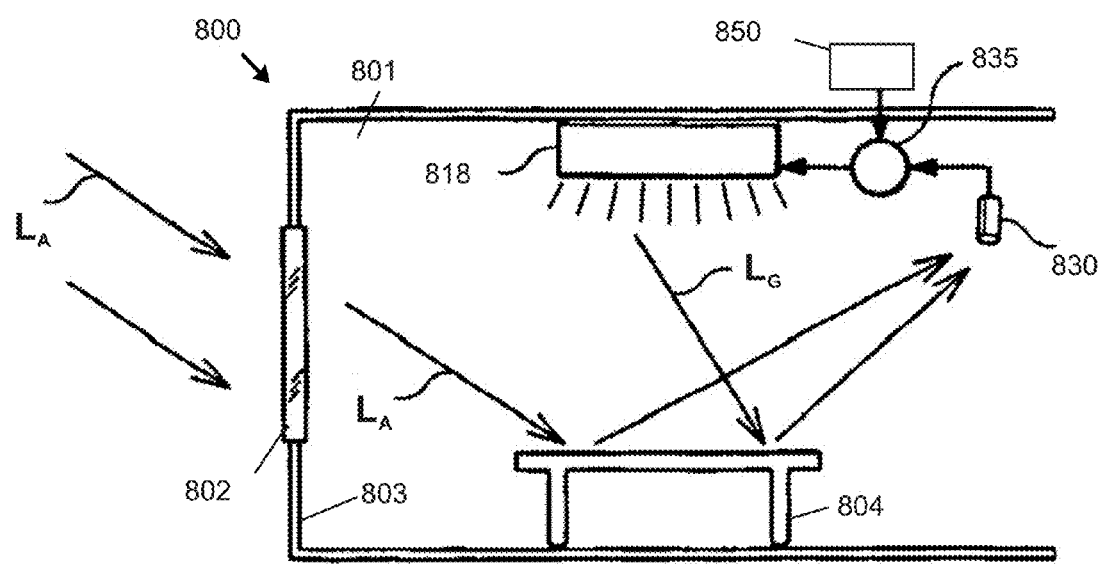
FIG. 19 is a schematic diagram of an interior space with a lighting device including multiple electrically activated emitters as described herein arranged to illuminate an indoor environment.

FIG. 19 is a schematic diagram of an interior space 800 with a lighting device 818 that may including multiple LED groups or arrays as described herein arranged to illuminate an indoor environment 801. The interior environment 801 may be bounded by walls 803 and may include a window 802 arranged to admit ambient light $L_A$. One or more objects (e.g., a table 804) may be arranged in the interior environment 801. One or more sensors 830 (e.g., photosensors) may be arranged to communicate sensory information (signals) to a controller 835 (which may include a driver module and/or a communication module) configured to control or affect operation of the lighting device 818, which outputs generated light $L_G$. One or more of sensor(s), a signal receiver, and a user input element 850 may also be provided to communicate signals to the controller 835 to affect operation of the lighting device 818. In certain embodiments, the preceding sensor(s), signal receiver, and/or user input element 850 may be remotely arranged relative to emitters of the lighting device 818, and may be arranged to communicate with the controller 835 via wired or wireless techniques. In certain embodiments, the preceding sensor(s), signal receiver, and/or user input element 850 are arranged to receive or determine information indicative of geospatial or geographic location (and optionally additional information such as time, time zone, and/or date), to permit the controller 835 to automatically adjust one or more light output parameters based at least in part on such information to operate electrically activated emitters of the lighting device 818 differently on different days of a year. In certain embodiments, one or more additional sensors 830 may also be exposed to the interior space 801 to be illuminated. In operation, ambient light $L_A$ may be transmitted through the window 802 into the interior space 801. Such ambient light $L_A$ may optionally combine with generated light $L_G$, optionally reflect from one or more surfaces or objects (e.g., table 804), and impinge on the one or more sensors 830. In certain embodiments, the one or more sensors 830 may include at least one light sensor. The sensor(s) 830 may be used to sense light intensity and/or color point, and output(s) of the sensor(s) 830 may be supplied to the controller 835. The controller 835 may be used to control operation of electrically activated emitters (e.g., LED groups) of the lighting device 818 to adjust light output parameters such as color point of emissions, color temperature of emissions, spectral content of emissions, luminous flux of emissions, and operating time.

Figure 20:
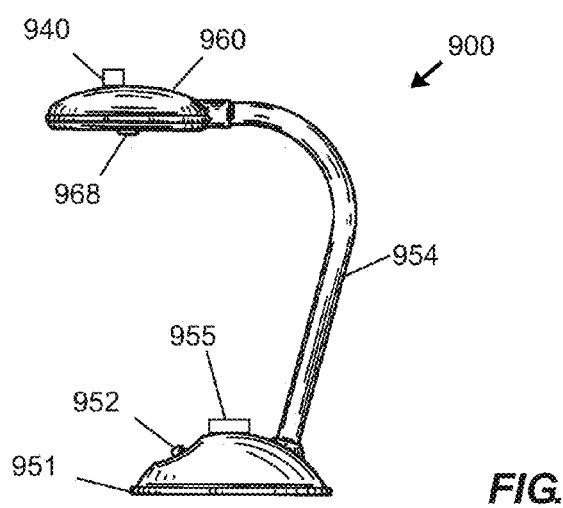
FIG. 20 is a side elevation view of a desk lamp or table lamp including multiple electrically activated emitters as described herein.

FIG. 20 illustrates an interior lamp (e.g., desk lamp or table lamp) 900 that may include multiple LED groups or arrays as described herein. The lamp 900 includes an arm 954 extending between a base 951 and a lamp head 960 that includes multiple LEDs 968. The base 951 may include a user input element 952 and a signal receiver 955, and the lamp head 960 may include one or more sensors 940. In certain embodiments, the preceding sensor(s) 940, signal receiver 955, and/or user input element 952 are configured arranged to receive or determine information indicative of geospatial or geographic location (and optionally additional information such as time, time zone, and/or date), to permit a driver module (not shown) to automatically adjust one or more light output parameters based at least in part on such information to operate the LEDs 968 differently on different days of a year. Light output parameters subject to adjustment may include I such as color point of emissions, color temperature of emissions, spectral content of emissions, luminous flux of emissions, and operating time.

Exemplary Applications for Lighting Devices or Lighting Systems Disclosed Herein In certain embodiments, a lighting device or lighting system as disclosed herein may be used to automatically determine or detect timing of sunrise and sunset (or daytime and nighttime conditions) for that location, with such timing being subject to change (e.g., from day to day) based upon seasonal variation.

In certain embodiments, a lighting device or lighting system as disclosed herein may be used to automatically determine or detect whether a particular day embodies a weekday or weekend, or embodies a holiday or non-holiday.

In certain embodiments, a lighting device or lighting system as disclosed herein may be used to automatically determine or detect zoning type (e.g., facility usage zoning) of a location in which the device or system is installed, with non-limiting examples of such zoning being business, retail, residential, school, industrial, or the like. In certain embodiments, zoning may be automatically determined with signals or information obtained from GPS, WiFi, cellular telephone, or similar signals, optionally aided by comparison to pre-defined databases, websites, or mapping systems that may include or permit derivation of zoning information for specific locations.

In certain embodiments, a lighting device or lighting system as disclosed herein may be used to automatically determine or detect whether a device or system is installed in an indoor location or an outdoor location. In certain embodiments, such determination may be made with one or more sensors, and/or such determination may be made with signals or information obtained from GPS, WiFi, cellular telephone, or similar signals, optionally aided by comparison to predefined databases, websites, or mapping systems.

In certain embodiments, a lighting device or lighting system as disclosed herein may be used to automatically determine or detect relative or absolute location of a lighting system or one or more lighting devices. In certain embodiments, such location information may include location of a room or space in which a lighting device or lighting system is located, location within a particular room of a lighting device or lighting system, location of one or more lighting devices relative to one or more other lighting devices, or location of a lighting device relative to one or more other objects. In certain embodiments, a lighting system or lighting device as disclosed herein may be used to detect movement of the lighting system or lighting device—for example, by communicating a signal via a network to a terminal or node arranged to receive information relating to the lighting system or lighting device.

In certain embodiments, a lighting system or lighting device as disclosed herein may be used to determine location of another object based upon information obtained or derived from a lighting device with location sensing ability. For example, an image sensor associated with a lighting device may be used to detect presence or absence of an other object in proximity to the lighting device, and such information coupled with geospatial location information for the lighting device may be used to determine location of the other object. In another example, an other object may be arranged to communicate wirelessly with one or more lighting devices, and presence of a signal, absence of a signal, strength of a signal, or triangulation of a signal between the other object and the one or more other lighting devices may be used to determine location of the other object.

Embodiments as disclosed herein may provide one or more of the following beneficial technical effects: permitting intensity and spectral content of artificial light to be automatically adjusted; easing the ability to program a lighting device to operate at an illumination level and spectral content suitable for a particular location, time, day of week, and season; facilitating maintenance of illumination of a brightness level and spectral content appropriate for the location, the time of day, the day of week, and the season; saving energy by operating artificial light sources that automatically compensate for presence, absence, intensity, and/or color point of natural ambient light; enhancing wellness of people exposed to light from artificial light sources; and permitting operation of a programmable lighting device to be adjusted according to long-term and instantaneous user preferences.

Various combinations and sub-combinations of the structures described herein are contemplated and will be apparent to a skilled person having knowledge of this disclosure. Any of the various features and elements as disclosed herein may be combined with one or more other disclosed features and elements unless indicated to the contrary herein.

Those skilled in the art will recognize improvements and modifications to the preferred embodiments of the present disclosure. All such improvements and modifications are considered within the scope of the concepts disclosed herein and the claims that follow.

What is claimed is:

1. A lighting device comprising:
   at least one electrically activated emitter;
   at least one element selected from: (a) a user input element, (b) a signal receiver, and (c) at least one sensor, wherein the at least one element is arranged to receive or provide at least one signal indicative of or permitting derivation of geospatial position; and
   a driver module arranged to adjust operation of the at least one electrically activated emitter differently on different days of a year based on the at least one signal and a predefined or user-defined schedule stored in a memory of the lighting device, wherein said adjustment alters spectral content of emissions of the lighting device, and wherein said predefined or user-defined schedule is configured to alter the spectral content of the emissions of the lighting device to compensate for yearly variations in spectral content of natural ambient light.

2. The lighting device of claim 1, wherein the at least one element is additionally arranged to receive or provide at least one signal indicative of or permitting derivation of any of date, time, and time zone.

3. The lighting device of claim 1, wherein the at least one element comprises a user input element arranged to provide at least one signal indicative of or permitting derivation of geospatial position.

4. The lighting device of claim 1, wherein the at least one element comprises a signal receiver arranged to receive at least one signal indicative of or permitting derivation of geospatial position.

5. The lighting device of claim 4, wherein the signal receiver comprises any of a GPS receiver, a radio frequency receiver, a WiFi receiver, a Bluetooth receiver, a ZigBee receiver, a modulated light receiver, an infrared receiver, and an encoded power line signal receiver.

6. The lighting device of claim 4, wherein the signal receiver is configured to wirelessly receive at least one signal indicative of or permitting derivation of geospatial position from a portable digital device or personal computer.

7. The lighting device of claim 1, wherein the at least one element comprises at least one sensor arranged to receive or provide at least one signal indicative of or permitting derivation of geospatial position.

8. The lighting device of claim 7, wherein the at least one sensor comprises any of an ambient light sensor and an image sensor.

9. The lighting device of claim 1, further comprising a body structure, wherein the at least one electrically activated emitter and the driver module are arranged in, mounted on, or supported by the body structure.

10. The lighting device of claim 9, wherein the at least one element is arranged in, mounted on, or supported by the body structure.

11. The lighting device of claim 1, wherein the at least one electrically activated emitter comprises a plurality of solid state light emitters.

12. The lighting device of claim 1, wherein said altering of spectral content of emissions of the lighting device alters at least one of the following: color point of emissions of the lighting device or color temperature of emissions of the lighting device.

13. A lighting system comprising:
    a plurality of lighting devices comprising a plurality of electrically activated emitters;
    at least one element selected from: (a) a user input element, (b) a signal receiver, and (c) at least one sensor, wherein the at least one element is arranged to receive or provide at least one signal indicative of or permitting derivation of geospatial position; and
    at least one driver module arranged to adjust operation of the plurality of electrically activated emitters differently on different days of a year based on the at least one signal and a predefined or user-defined schedule stored in a memory of the lighting system, wherein said adjustment alters spectral content of emissions of the lighting system, and wherein said predefined or user-defined schedule is configured to alter the spectral content of the emissions of the lighting system to compensate for yearly variations in spectral content of natural ambient light.

14. The lighting system of claim 13, wherein the at least one element is additionally arranged to receive or provide at least one signal indicative of or permitting derivation of any of date, time, and time zone.

15. The lighting system of claim 13, wherein the at least one element comprises a user input element arranged to provide at least one signal indicative of or permitting derivation of geospatial position.

16. The lighting system of claim 13, wherein the at least one element comprises a signal receiver arranged to receive at least one signal indicative of or permitting derivation of geospatial position.

17. The lighting system of claim 16, wherein the signal receiver comprises any of a GPS receiver, a radio frequency receiver, a WiFi receiver, a Bluetooth receiver, a ZigBee receiver, a modulated light receiver, an infrared receiver, and an encoded power line signal receiver.

18. The lighting system of claim 13, wherein the at least one element comprises at least one sensor arranged to receive or provide at least one signal indicative of or permitting derivation of geospatial position.

19. The lighting system of claim 13, wherein the plurality of lighting devices includes a first lighting device comprising at least one first group of solid state light emitters and a second lighting device comprising at least one second group of solid state light emitters.

20. The lighting system of claim 19, wherein the first lighting device includes a signal transmitter arranged to transmit at least one signal indicative of or permitting derivation of geospatial position from the first lighting device to the second lighting device.

21. The lighting system of claim 19, wherein the at least one driver module comprises a first driver module associated with the first lighting device and comprises a second driver module associated with the second lighting device, wherein the first driver module is arranged to drive the at least one first group of solid state light emitters, and the second driver module is arranged to drive the at least one second group of solid state light emitters.

22. The lighting system of claim 13, wherein the at least one element is located remotely from each lighting device of the plurality of lighting devices.

23. The lighting system of claim 13, wherein said altering of spectral content of emissions of the lighting system alters at least one of the following: color point of emissions of the lighting system or color temperature of emissions of the lighting system.

24. A lighting system comprising:
at least one element selected from: (a) a user input element, (b) a signal receiver, and (c) at least one sensor, wherein the at least one element is arranged to receive or provide at least one first signal indicative of or permitting derivation of geospatial position;
a first lighting device comprising at least one first electrically activated emitter, a wireless transmitter arranged to transmit at least one second signal derived from or including at least a portion of the at least one first signal, and a first driver module arranged to adjust operation of the at least one first electrically activated emitter differently on different days of a year based on the at least one first signal and a first predefined or user-defined schedule stored in a memory of the first lighting device, wherein said adjustment of operation of the at least one first electrically activated emitter alters spectral content of emissions of the first lighting device, and wherein said first predefined or user-defined schedule is configured to alter the spectral content of the emissions of the first lighting device to compensate for yearly variations in spectral content of natural ambient light; and
a second lighting device comprising at least one second electrically activated emitter, a receiver arranged to receive the at least one second signal from the wireless transmitter, and a second driver module arranged to adjust operation of the at least one second electrically activated emitter differently on different days of a year based on the at least one second signal and a second predefined or user-defined schedule stored in a memory of the second lighting device, wherein said adjustment of operation of the at least one second electrically activated emitter alters spectral content of emissions of the second lighting device, and wherein said second predefined or user-defined schedule is configured to alter the spectral content of the emissions of the second lighting device to compensate for yearly variations in the spectral content of natural ambient light.

25. The lighting system of claim 24, wherein the at least one element is additionally arranged to receive or provide at least one first signal indicative of or permitting derivation of any of date, time, and time zone.

26. The lighting system of claim 24, wherein the at least one element comprises a user input element arranged to provide at least one first signal indicative of or permitting derivation of geospatial position.

27. The lighting system of claim 24, wherein the at least one element comprises a signal receiver arranged to receive at least one first signal indicative of or permitting derivation of geospatial position.

28. The lighting system of claim 27, wherein the signal receiver comprises any of a GPS receiver, a radio frequency receiver, a WiFi receiver, a Bluetooth receiver, a ZigBee receiver, a modulated light receiver, an infrared receiver, and an encoded power line signal receiver.

29. The lighting system of claim 24, wherein the at least one element comprises at least one sensor arranged to receive or provide at least one first signal indicative of or permitting derivation of geospatial position.

30. The lighting system of claim 24, wherein said altering of spectral content of emissions of the first lighting device alters at least one of the following: color point of emissions of the first lighting device or color temperature of emissions of the first lighting device, and wherein said altering of spectral content of emissions of the second lighting device alters at least one of the following: color point of emissions of the second lighting device or color temperature of emissions of the second lighting device.

31. A method for operating a lighting device including at least one electrically activated emitter, the method comprising:
receiving by the lighting device, or providing to the lighting device, at least one signal indicative of or permitting derivation of geospatial position;
establishing a predefined or user-defined schedule configured to adjust operation of the at least one electrically activated emitter differently on different days of a year to compensate for yearly variations in spectral content of natural ambient light based on the at least one signal, wherein said adjustment of operation alters spectral content of emissions of the lighting device; and
operating the at least one electrically activated emitter of the lighting device differently on different days of a year according to the predefined or user-defined schedule.

32. The method of claim 31, further comprising:
sensing any of an ambient light condition, a condition of an illuminated space or surface, and a weather condition; and
responsive to said sensing, performing intraday adjustment of at least one of brightness or spectral content of light emissions of the lighting device to modify operation relative to operation of the lighting device specified in the predefined or user-defined schedule.

33. The method of claim 31, further comprising:
receiving by the lighting device, or providing to the lighting device, at least one signal indicative of or permitting derivation of at least one of date or time; and
altering the predefined or user-defined schedule based on the at least one of date or time.

34. The method of claim 31, wherein the at least one signal indicative of or permitting derivation of geospatial position is received by or provided by at least one element selected from: (a) a user input element, (b) a signal receiver, and (c) at least one sensor.

35. The method of claim 31, wherein said altering of spectral content of emissions of the lighting device alters at least one of the following: color point of emissions of the lighting device or color temperature of emissions of the lighting device.

* * * * *